(12) United States Patent
Ting et al.

(10) Patent No.: US 7,220,735 B2
(45) Date of Patent: May 22, 2007

(54) BENZIMIDAZOLONE HISTAMINE $H_3$ ANTAGONISTS

(75) Inventors: Pauline C. Ting, New Providence, NJ (US); Robert G. Aslanian, Rockaway, NJ (US); Michael Y. Berlin, Flemington, NJ (US); Christopher W. Boyce, Flemington, NJ (US); Jianhua Cao, Scotch Plains, NJ (US); Pietro Mangiaracina, Monsey, NY (US); Kevin D. McCormick, Edison, NJ (US); Mwangi W. Mutahi, Orange, NJ (US); Stuart B. Rosenblum, West Orange, NJ (US); Neng-Yang Shih, North Caldwell, NJ (US); Daniel M. Solomon, Edison, NJ (US); Wing C. Tom, Cedar Grove, NJ (US); Qingbei Zeng, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 482 days.

(21) Appl. No.: 10/414,943

(22) Filed: Apr. 16, 2003

(65) Prior Publication Data

US 2004/0048843 A1    Mar. 11, 2004

Related U.S. Application Data

(60) Provisional application No. 60/373,467, filed on Apr. 18, 2002.

(51) Int. Cl.
*A61K 31/495*    (2006.01)

(52) U.S. Cl. ............. 514/210.21; 544/224; 544/336; 546/184; 546/192; 546/193; 546/194

(58) Field of Classification Search ........... 514/210.21; 544/224, 336; 546/184, 192, 193, 194
See application file for complete search history.

(56) References Cited

U.S. PATENT DOCUMENTS

| | | | |
|---|---|---|---|
| 5,807,865 A | 9/1998 | Harrison et al. | |
| 5,869,479 A | 2/1999 | Kreutner et al. | ............ 514/212 |
| 6,211,199 B1 | 4/2001 | Kane et al. | |

FOREIGN PATENT DOCUMENTS

| | | |
|---|---|---|
| CA | 2387613 | 5/2001 |
| JP | 63-227573 | 9/1988 |
| WO | 96/13262 | 5/1996 |
| WO | WO 98/06394 | 2/1998 |
| WO | 01/32649 | 5/2001 |
| WO | 02/24659 | 3/2002 |
| WO | WO 02/32893 | 4/2002 |
| WO | WO 02/072570 | 9/2002 |
| WO | 02/085890 | 10/2002 |

OTHER PUBLICATIONS

"Abbott's H3 histamine receptor antagonist, ABT-239, a candidate treatment of cognitive disorders, ADHD, Alzheimer's and schizophrenia," TherapeuticAdvances Lead Discovery's bulletin, www.leaddiscovery.co.uk, Jan. 2005, pp. 1-5.*
Basic Clinical and Pharmacology, 7th edition, Bertram G. Katzung, pp. 268-269.*
Henning et al., *Journal of Medicinal Chemistry*, vol. 30, 1987, pp. 814-819.
Curtin et al., *Journal of Medicinal Chemistry*, vol. 41 (1998) pp. 74-95.
Obase et al., *J. Heterocyclic Chemistry*, vol. 20 (1983) pp. 565-573.
Rizzo et al., *European Journal of Pharmacology*, vol. 294 (1995) pp. 329-335.
McLeod et al, Combined Histamine H1 and H3 . . . Am. J. Rhinology, 13, 5 (1999), p. 391-399.
Taylor-Clark et al, Histamine Receptors . . . , Brit J. Pharmacology, 144 (2005), p. 657-674.
Leura et al, Therapeutic potential of histamine . . . , TiPS, 19 (1998), p. 177-183.
Henning et al., *Journal of Medicinal Chemistry*, vol. 30, 1987, pp. 814-819.
Curtain et al., *Journal of Medicinal Chemistry*, vol. 41 (1998) pp. 74-95.
Obase et al., *J. Heterocyclic Chemistry*, vol. 20 (1983) pp. 565-573.
Rizzo et al., *European Journal of Pharmacology*, vol. 294 (1995) pp. 329-335.
U.S. Appl. No. 10/417,391.
U.S. Appl. No., filed Jun. 20, 2003, "Indole Derivatives Useful as Histamine $H_3$ Antagonists" (claims benefit of 60/390,987).
CA 137:337920, 2002:832786 (abstract of WO 02/085890).

* cited by examiner

*Primary Examiner*—James O. Wilson
*Assistant Examiner*—Jason H. Johnsen
(74) *Attorney, Agent, or Firm*—Anita W. Magatti; Jeffrey P. Bergman

(57) ABSTRACT

Disclosed are novel compounds of the formula

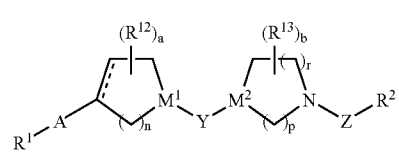

I wherein $R^1$ is benzimidazolone derivative, $M^1$ and $M^2$ are optionally substituted carbon or nitrogen, $R^2$ includes optionally substituted aryl or heteroaryl, and the remaining variables are as defined in the specification, and the remaining variables are as defined in the specification; also disclosed are pharmaceutical compositions comprising the compounds of formula I and methods of treating various diseases or conditions, such as allergy, allergy-induced airway responses, and congestion (e.g., nasal congestion) using the compounds of formula I, as well as methods of treating said diseases or conditions using the compounds of formula I in combination with an $H_1$ receptor antagonist.

18 Claims, No Drawings

BENZIMIDAZOLONE HISTAMINE $H_3$ ANTAGONISTS

CROSS REFERENCE TO RELATED APPLICATION

This application claims the benefit of U.S. Provisional Application 60/373,467, filed Apr. 18, 2002.

FIELD OF THE INVENTION

The present invention relates to novel substituted benzimidazolones, and aza- and diaza-derivatives thereof, useful as histamine $H_3$ antagonists. The invention also relates to pharmaceutical compositions comprising said compounds and their use in treating inflammatory diseases, allergic conditions and central nervous system disorders. The invention also relates to the use of a combination of novel histamine $H_3$ antagonists of this invention with histamine $H_1$ compounds for the treatment of inflammatory diseases and allergic conditions, as well as pharmaceutical compositions comprising a combination of one or more novel histamine $H_3$ antagonist compounds of the invention with one or more histamine $H_1$ compounds.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates nonepinephrine outflow to resistance and capacitance vessels, causing vasodilation.

Imidazole $H_3$ receptor antagonists are well known in the art. More recently, non-imidazole $H_3$ receptor antagonists have been disclosed in WO 02/32893 and WO 02/072,570.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

SUMMARY OF THE INVENTION

The present invention provides novel compounds of formula I:

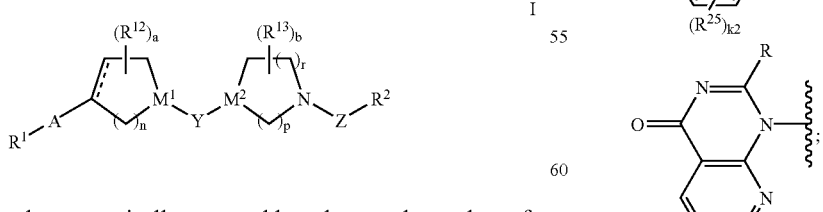

or a pharmaceutically acceptable salt or solvate thereof, wherein:
the dotted line represents an optional double bond;
a is 0 to 3;
b is 0 to 3;
n is 1, 2 or 3;
p is 1, 2 or 3 with the proviso that when $M^2$ is N, then p is not 1;
r is 1, 2, or 3 with the proviso that when r is 2 or 3, then $M^2$ is $C(R^3)$ and p is 2 or 3;
A is a bond or $C_1$–$C_6$ alkylene;
$M^1$ is $C(R^3)$ or N;
$M^2$ is $C(R^3)$ or N;
Y is —C(=O)—, —C(=S)—, —$(CH_2)_q$—, —$NR^4C$(=O)—, —C(=O)$NR^4$—, —C(=O)$CH_2$—, —$CH_2$(C=O)—, —$SO_{1-2}$—, —NH—C(=N—CN)— or —C(=N—CN)—NH—; with the provisos that when $M^1$ is N, Y is not —$NR^4C$(=O)— or —NH—C(=N—CN)—; and when $M^2$ is N, Y is not —C(=O)$NR^4$— or —C(=N—CN)—NH—;
q is 1 to 5, provided that when $M^1$ and $M^2$ are both N, q is not 1;
Z is a bond, $C_1$–$C_6$ alkylene, $C_1$–$C_6$ alkenylene, —C(=O)—, —CH(CN)—, or —$CH_2$C(=O)$NR^4$—;
$R^1$ is

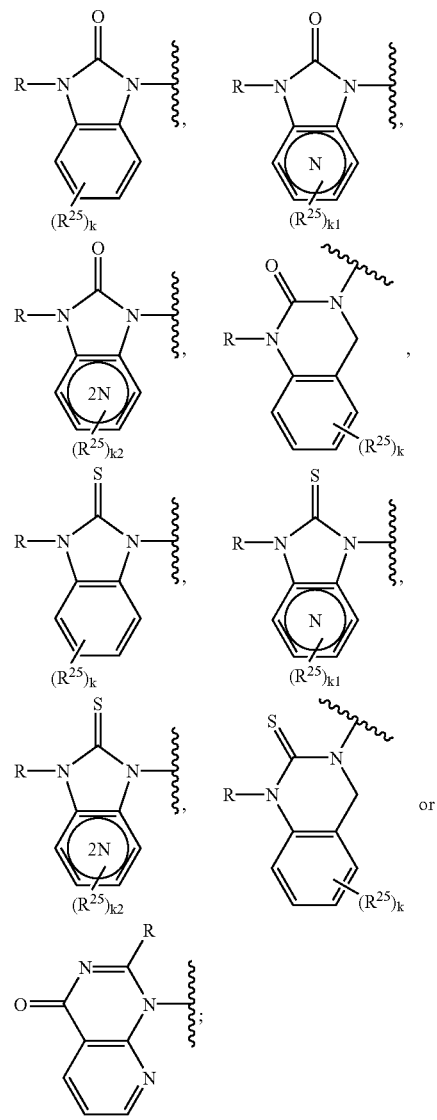

k is 0, 1, 2, 3 or 4;
k1 is 0, 1, 2 or 3;
k2 is 0, 1 or 2;

R is H, $C_1$–$C_6$ alkyl, hydroxy-($C_2$–$C_6$)alkyl-, halo-($C_1$–$C_6$)alkyl-, halo-($C_1$–$C_6$)-alkoxy-($C_1$–$C_6$)alkyl-, $R^{29}$—O—C(O)—($C_1$–$C_6$)alkyl-, ($C_1$–$C_6$)alkoxy-($C_1$–$C_6$)alkyl-, $N(R^{30})(R^{31})$—($C_1$–$C_6$)alkyl-, ($C_1$–$C_6$)alkoxy-($C_1$–$C_6$)alkoxy-($C_1$–$C_6$)alkyl-, $R^{32}$-aryl, $R^{32}$-aryl($C_1$–$C_6$)alkyl-, $R^{32}$-aryloxy($C_1$–$C_6$)alkyl-, $R^{32}$-heteroaryl, $R^{32}$-heteroaryl($C_1$–$C_6$)alkyl-, ($C_3$–$C_6$)cycloalkyl, ($C_3$–$C_6$)cycloalkyl($C_1$–$C_6$)alkyl-, $N(R^{30})(R^{31})$—C(O)—($C_1$–$C_6$)alkyl-, or heterocycloalkyl($C_1$–$C_6$)alkyl-;

$R^2$ is a six-membered heteroaryl ring having 1 or 2 heteroatoms independently selected from N or N—O, with the remaining ring atoms being carbon; a five-membered heteroaryl ring having 1, 2, 3 or 4 heteroatoms independently selected from N, O or S, with the remaining ring atoms being carbon; $R^{32}$-quinolyl; $R^{32}$-aryl; heterocycloalkyl; ($C_3$–$C_6$)cycloalkyl; ($C_1$–$C_6$)alkyl; hydrogen;

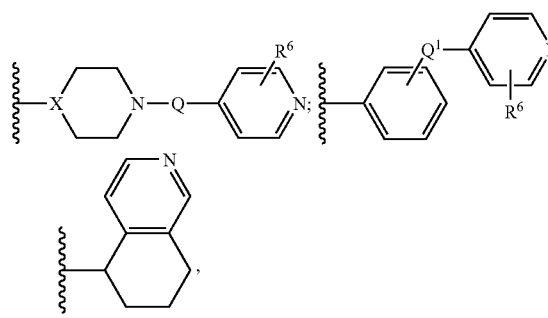

wherein said six-membered heteroaryl ring or said five-membered heteroaryl ring is optionally substituted by $R^6$;

X is CH or N;

Q is a bond or $C_1$–$C_6$ alkylene;

$Q^1$ is a bond, $C_1$–$C_6$ alkylene or —N($R^4$)—;

$R^3$ is H, halogen, $C_1$–$C_6$ alkyl, —OH or ($C_1$–$C_6$)alkoxy;

$R^4$ is independently selected from the group consisting of hydrogen, $C_1$–$C_6$ alkyl, $C_3$–$C_6$ cycloalkyl, ($C_3$–$C_6$)cycloalkyl($C_1$–$C_6$)alkyl, $R^{33}$-aryl, $R^{33}$-aryl($C_1$–$C_6$)alkyl, and $R^{32}$-heteroaryl;

$R^5$ is hydrogen, $C_1$–$C_6$ alkyl, —C(O)$R^{20}$, —C(O)$_2R^{20}$, —C(O)N($R^{20}$)$_2$ or ($C_1$–$C_6$)alkyl-SO$_2$—;

or $R^4$ and $R^5$, together with the nitrogen to which they are attached, form an azetidinyl, pyrrolidinyl, piperidinyl, piperazinyl or morpholinyl ring;

$R^6$ is 1 to 3 substituents independently selected from the group consisting of —OH, halogen, $C_1$–$C_6$ alkyl-, $C_1$–$C_6$ alkoxy, $C_1$–$C_6$ alkylthio, —CF$_3$, —NR$^4$R$^5$, NO$_2$, —CO$_2$R$^4$, —CON(R$^4$)$_2$, —CH$_2$—NR$^4$R$^5$, —CN,

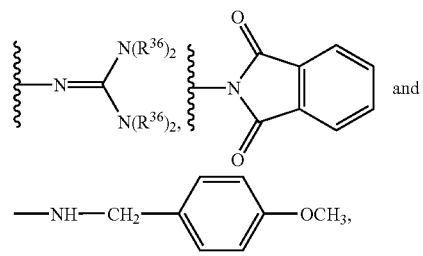

—NH—CH$_2$—⟨phenyl⟩—OCH$_3$, or 2 $R^6$ substituents together on the same carbon are =O;

$R^{12}$ is independently selected from the group consisting of $C_1$–$C_6$ alkyl, hydroxy, $C_1$–$C_6$ alkoxy, or fluoro, provided that when $R_{12}$ is hydroxy or fluoro, then $R^{12}$ is not bound to a carbon adjacent to a nitrogen; or two $R^{12}$ substituents together form a $C_1$ to $C_2$ alkyl bridge from one ring carbon to another non-adjacent ring carbon; or $R^{12}$ is =O;

$R^{13}$ is independently selected from the group consisting of $C_1$–$C_6$ alkyl, hydroxy, $C_1$–$C_6$ alkoxy, or fluoro, provided that when $R^{13}$ is hydroxy or fluoro then $R^{13}$ is not bound to a carbon adjacent to a nitrogen; or two $R^{13}$ substituents together form a $C_1$ to $C_2$ alkyl bridge from one ring carbon to another non-adjacent ring carbon; or $R^{13}$ is =O;

$R^{20}$ is independently selected from the group consisting of hydrogen, $C_1$–$C_6$ alkyl, or aryl, wherein said aryl group is optionally substituted with from 1 to 3 groups independently selected from halogen, —CF$_3$, —OCF$_3$, hydroxyl, or methoxy; or when two $R^{20}$ groups are present, said two $R^{20}$ groups taken together with the nitrogen to which they are bound can form a five or six membered heterocyclic ring;

$R^{22}$ is $C_1$–$C_6$ alkyl, $R^{34}$-aryl or heterocycloalkyl;

$R^{24}$ is H, $C_1$–$C_6$ alkyl, —SO$_2R^{22}$ or $R^{34}$-aryl;

$R^{25}$ is independently selected from the group consisting of $C_1$–$C_6$ alkyl, —CN, —NO$_2$, halogen, —CF$_3$, —OH, $C_1$–$C_6$ alkoxy, ($C_1$–$C_6$)alkyl-C(O)—, aryl-C(O)—, N(R$^4$)(R$^5$)—C(O)—, N(R$^4$)(R$^5$)—S(O)$_{1-2}$, halo-($C_1$–$C_6$)alkyl- or halo-($C_1$–$C_6$)alkoxy-($C_1$–$C_6$)alkyl-;

$R^{29}$ is H, $C_1$–$C_6$ alkyl, $R^{35}$-aryl or $R^{35}$-aryl($C_1$–$C_6$)alkyl-;

$R^{30}$ is H, $C_1$–$C_6$ alkyl-, $R^{35}$-aryl or $R^{35}$-aryl($C_1$–$C_6$)alkyl-;

$R^{31}$ is H, $C_1$–$C_6$ alkyl-, $R^{35}$-aryl, $R^{35}$-aryl($C_1$–$C_6$)alkyl-, ($C_1$–$C_6$)alkyl-C(O)—, $R^{35}$-aryl-C(O)—, N(R$^4$)(R$^5$)—C(O)—, ($C_1$–$C_6$)alkyl-S(O)$_2$— or $R^{35}$-aryl-S(O)$_2$—;

or $R^{30}$ and $R^{31}$ together are —(CH$_2$)$_{4-5}$—, —(CH$_2$)$_2$—O—(CH$_2$)$_2$— or —(CH$_2$)$_2$—N(R$^{29}$)—(CH$_2$)$_2$— and form a ring with the nitrogen to which they are attached;

$R^{32}$ is 1 to 3 substituents independently selected from the group consisting of H, —OH, halogen, $C_1$–$C_6$ alkyl, $C_1$–$C_6$ alkoxy, —SR$^{22}$, —CF$_3$, —OCF$_3$, —OCHF$_2$, —NR$^{37}$R$^{38}$, —NO$_2$, —CO$_2R^{37}$, —CON(R$^{37}$)$_2$, —S(O)$_2R^{22}$, —S(O)$_2$N(R$^{20}$)$_2$, —N(R$^{24}$)S(O)$_2R^{22}$, —CN, hydroxy-($C_1$–$C_6$)alkyl- and —OCH$_2$CH$_2$OR$^{22}$;

$R^{33}$ is 1 to 3 substituents independently selected from the group consisting of $C_1$–$C_6$ alkyl, halogen, —CN, —NO$_2$, —OCHF$_2$ and —O—($C_1$–$C_6$)alkyl;

$R^{34}$ is 1 to 3 substituents independently selected from the group consisting of H, halogen, —CF$_3$, —OCF$_3$, —OH and —OCH$_3$;

$R^{35}$ is 1 to 3 substituents independently selected from hydrogen, halo, $C_1$–$C_6$ alkyl, hydroxy, $C_1$–$C_6$ alkoxy, phenoxy, —CF$_3$, —N(R$^{36}$)$_2$, —COOR$^{20}$ and —NO$_2$;

$R^{36}$ is independently selected form the group consisting of H and $C_1$–$C_6$ alkyl;

$R^{37}$ is independently selected from the group consisting of hydrogen, $C_1$–$C_6$ alkyl, $C_3$–$C_6$ cycloalkyl, ($C_3$–$C_6$)cycloalkyl($C_1$–$C_6$)alkyl, $R^{33}$-aryl, $R^{33}$-aryl($C_1$-$C_6$)alkyl, and $R^{32}$-heteroaryl; and $R^{38}$ is hydrogen, $C_1$–$C_6$ alkyl, —C(O)R$^{20}$, —C(O)$_2R^{20}$, —C(O)N(R$^{20}$)$_2$ or ($C_1$–$C_6$)alkyl-SO$_2$—;

or $R^{37}$ and $R^{38}$, together with the nitrogen to which they are attached, form an azetidinyl, pyrrolidinyl, piperidinyl, piperazinyl or morpholinyl ring.

This invention also provides a pharmaceutical composition comprising an effective amount of compound of at least one compound of formula I and a pharmaceutically acceptable carrier.

This invention further provides a method of treating allergy, allergy-induced airway (e.g., upper airway) responses, congestion (e.g., nasal congestion), hypotension, cardiovascular disease, diseases of the GI tract, hyper- and hypo-motility and acidic secretion of the gastro-intestinal tract, obesity, sleeping disorders (e.g., hypersomnia, somnolence, and narcolepsy), disturbances of the central nervous system, attention deficit hyperactivity disorder (ADHD), hypo and hyperactivity of the central nervous system (for example, agitation and depression), and/or other CNS disorders (such as Alzheimer's, schizophrenia, and migraine) comprising administering to a patient in need of such treatment an effective amount of at least one compound of formula I.

Compounds of this invention are particularly useful for treating allergy, allergy-induced airway responses and/or congestion.

This invention further provides a pharmaceutical composition comprising an effective amount of a combination of at least one compound of formula I and at least one $H_1$ receptor antagonist in combination with a pharmaceutically acceptable carrier.

This invention further provides a method of treating allergy, allergy-induced airway (e.g., upper airway) responses, and/or congestion (e.g., nasal congestion) comprising administering to a patient in need of such treatment (e.g., a mammal, such as a human being) an effective amount of a combination of at least one compound of formula I and at least one $H_1$ receptor antagonist.

Kits comprising a compound of formula I in a pharmaceutical composition, and a separate $H_1$ receptor antagonist in a pharmaceutical compositions in a single package are also contemplated.

DETAILED DESCRIPTION OF THE INVENTION

Preferred definitions of the variables in the structure of formula I are as follows:

$R^1$ is preferably R-substituted benzimidazolone, wherein R is preferably H, alkyl, alkoxyalkyl, $R^{32}$-aryl, $R^{32}$-heteroaryl or heterocycloalkylalkyl. More preferably, R is —$CH_3$, phenyl, 4-fluorophenyl, $CH_3$—O—$(CH_2)_2$—,

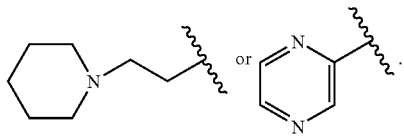

$R^{25}$ is preferably halogen or —$CF_3$ and k is 0 or 1. When $R^1$ is an aza- or diaza derivative of benzimidazolone, R is preferably as defined for benzimidazolone, and $k_1$ and $k_2$ are preferably zero.

$R^2$ is preferably a six-membered heteroaryl ring, optionally substituted with one substituent. More preferably, $R^2$ is pyridyl, pyrimidinyl or pyridazinyl, each optionally substituted with halogen or —$NR^4R^5$, wherein $R^4$ and $R^5$ are independently selected from the group consisting of H and ($C_1$–$C_6$)alkyl, or $R^4$ and $R^5$ together with the nitrogen to which they are attached form a pyrrolidinyl, piperidinyl or morpholinyl ring.

A is preferably a bond.

Y is preferably —C(O)—.

Z is preferably straight or branched $C_1$–$C_3$ alkyl.

$M^1$ is preferably N; a is preferably 0; and n is preferably 2; the optional double bond is preferably not present (i.e., a single bond is present).

$M^2$ is preferably $C(R^3)$ wherein $R^3$ is hydrogen or halogen, especially fluorine; b is preferably 0; r is preferably 1; and p is preferably 2.

As used herein, the following terms have the following meanings, unless indicated otherwise:

alkyl (including, for example, the alkyl portions of arylalkyl and alkoxy) represents straight and branched carbon chains and contains from one to six carbon atoms;

alkylene represents a divalent straight or branched alkyl chain, e.g., ethylene (—$CH_2CH_2$—) or propylene (—$CH_2CH_2CH_2$—);

Haloalkyl or haloalkoxy represent alkyl or alkoxy chains as defined above wherein one or more hydrogen atoms are replaced by halogen atoms, e.g., —$CF_3$, $CF_3CH_2CH_2$—, $CF_3CF_2$— or $CF_3O$—;

aryl (including the aryl portion of arylalkyl) represents a carbocyclic group containing from 6 to 14 carbon atoms and having at least one aromatic ring (e.g., aryl is a phenyl or naphthyl ring), with all available substitutable carbon atoms of the carbocyclic group being intended as possible points of attachment;

arylalkyl represents an aryl group, as defined above, bound to an alkyl group, as defined above, wherein said alkyl group is bound to the compound;

cycloalkyl represents saturated carbocyclic rings of from 3 to 6 carbon atoms;

halogen (halo) represents fluoro, chloro, bromo and iodo;

heteroaryl represents cyclic groups, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms; examples include but are not limited to isothiazolyl, isoxazolyl, oxazolyl, furazanyl, triazolyl, tetrazolyl, thiazolyl, thiadiazolyl, isothiadiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoquinolinyl, quinolinyl, naphthyridinyl; the 5- and 6-membered heteroaryl groups included in the definition of $R^2$ are exemplified by the heteroaryl groups listed above; all available substitutable carbon and nitrogen atoms can be substituted as defined.

heterocycloalkyl represents a saturated, carbocyclic ring containing from 3 to 15 carbon atoms, preferably from 4 to 6 carbon atoms, which carbocyclic ring is interrupted by 1 to 3 hetero groups selected from —O—, —S—, —SO—, —$SO_2$ or —$NR^{40}$— wherein $R^{40}$ represents H, $C_1$ to $C_6$ alkyl, arylalkyl, —$C(O)R^{20}$, —$C(O)OR^{20}$, or —C(O)N $(R^{20})_2$ (wherein each $R^{20}$ is independently selected); examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperazinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl.

When $R^{12}$ or $R^{13}$ is said to be =O, this means that two hydrogen atoms on the same carbon atom of the ring can be replaced by =O. When two $R^{12}$ or $R^{13}$ groups are said to form a bridge between non-adjacent carbon atoms, the bridge will not include carbon atoms in $M^1$ or $M^2$, not the carbon joined to "A". An example of a bridged ring is

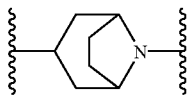

for example in the structure

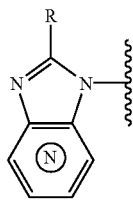

represents a nitrogen atom that is located at one of the 4 non-fused positions of the ring, i.e., positions 4, 5, 6 or 7 indicated below:

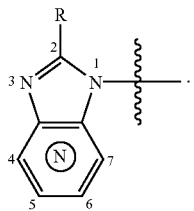

Similarly,

means that two nitrogens are located at any two of the 4 non-fused positions of the ring, e.g., the 4 and 6 positions, the 4 and 7 positions, or the 5 and 6 positions.

"Patient" means a mammal, typically a human, although veterinary use is also contemplated.

Also, as used herein, "upper airway" usually means the upper respiratory system—i.e., the nose, throat, and associated structures.

Also, as used herein, "effective amount" generally means a therapeutically effective amount.

A line drawn into a ring means that the indicated bond may be attached to any of the substitutable ring carbon atoms.

Certain compounds of the invention may exist in different isomeric (e.g., enantiomeric, diastereoisomeric and geometric) forms. The invention contemplates all such isomers both in pure form and in admixture, including racemic mixtures. Enol forms and tautomers are also included.

The compounds of this invention are ligands for the histamine $H_3$ receptor. The compounds of this invention can also be described as antagonists of the $H_3$ receptor, or as $H_3$ antagonists.

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms can differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases. Thus, for example, if there is a carboxylic acid substituent in the molecule, a salt may be formed with an inorganic as well as organic base such as, for example, NaOH, KOH, $NH_4OH$, tetraalkylammonium hydroxide, and the like.

The compounds of formula I can exist in unsolvated as well as solvated forms, including hydrated forms, e.g., hemi-hydrate. In general, the solvated form, with pharmaceutically acceptable solvents such as water, ethanol and the like are equivalent to the unsolvated form for purposes of the invention.

The compounds of this invention can be combined with an $H_1$ receptor antagonist (i.e., the compounds of this invention can be combined with an $H_1$ receptor antagonist in a pharmaceutical composition, or the compounds of this invention can be administered with an $H_1$ receptor antagonist).

Numerous chemical substances are known to have histamine $H_1$ receptor antagonist activity and can therefore be used in the methods of this invention. Many $H_1$ receptor antagonists useful in the methods of this invention can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole.

Even more preferably, said $H_1$ antagonist is selected from loratadine, descarboethoxyloratadine, fexofenadine or cetirizine. Most preferably, said $H_1$ antagonist is loratadine or descarboethoxyloratadine.

In one preferred embodiment, said $H_1$ receptor antagonist is loratadine.

In another preferred embodiment, said $H_1$ receptor antagonist is descarboethoxyloratadine.

In still another preferred embodiment, said $H_1$ receptor antagonist is fexofenadine.

In yet another preferred embodiment, said $H_1$ receptor antagonist is cetirizine.

Preferably, in the above methods, allergy-induced airway responses are treated.

Also, preferably, in the above methods, allergy is treated.

Also, preferably, in the above methods, nasal congestion is treated.

In the methods of this invention wherein a combination of an $H_3$ antagonist of this invention (compound of formula I) is administered with an $H_1$ antagonist, the antagonists can be administered simultaneously or sequentially (first one and then the other over a period of time). In general, when the antagonists are administered sequentially, the $H_3$ antagonist of this invention (compound of formula I) is administered first.

Compounds of the present invention can be prepared by a number of ways evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps has to be controlled to avoid functional group incompatibilities. One such method for the preparation of compounds of formula I wherein $R^1$ is benzimidazolone is shown in Scheme 1 below. Similar procedures can be used to prepare the aza-benzimidazolones (i.e., compounds wherein $R^1$ is other than benzimidazolone as defined above) and $R^{25}$-substituted benzimidazolones and aza-benzimidazolones. In the scheme, Prot is a protecting group and the variables are as defined above or in the following description.

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Henning et al have reported a synthesis of compounds XIV in Scheme I, below, where $M^1$ of formula I is a nitrogen atom in $J.$ $Med.$ $Chem.$ 30, (1987) 814.

One skilled in the art will recognize that the synthesis of compounds of formula XVI may require the need for the protection of certain functional groups (i.e. derivatization for the purpose of chemical compatibility with a particular reaction condition). Suitable protecting groups for an amine are methyl, benzyl, ethoxyethyl, t-butoxycarbonyl, phthaloyl and the like which can appended to and removed by literature methods known to those skilled in the art.

One skilled in the art will recognize that the synthesis of compounds of formula XVI may require the construction of an amide bond. Methods include but are not limited to the use of a reactive carboxy derivative (e.g. acid halide) or the use of an acid with a coupling reagent (e.g. DECI, DCC) with an amine at 0° C. to 100° C. Suitable solvents for the reaction are halogenated hydrocarbons, ethereal solvents, dimethylformamide and the like.

One skilled in the art will recognize that the synthesis of compounds of formula XVI may require the construction of an amine bond. Methods include but are not limited to the reaction of an amine with a reactive carbonyl (e.g. aldehyde or ketone) under reductive amination conditions. Suitable reducing reagents for the reaction include $NaBH_3CN$, sodium triacetoxyborohydride and the like at 0° C. to 100° C. Suitable solvents for the reaction are halogenated hydrocarbons, ethereal solvents, dimethylformamide and the like.

One skilled in the art will recognize that the synthesis of compounds of formula XVI may require the reduction of a reducible functional group. Suitable reducing reagents include $NaBH_4$, $LiAlH_4$, diborane and the like at −20° C. to 100° C. Suitable solvents for the reaction are halogenated hydrocarbons, ethereal solvents, dimethylformamide, alcohols and alike.

One skilled in the art will recognize that the synthesis of compounds of formula XVI may require the oxidation of a functional group. Suitable oxidizing reagents include oxygen, hydrogen peroxide, m-chloroperoxybenzoic acid and the like at −20° C. to 100° C. Suitable solvents for the reaction are halogenated hydrocarbons, ethereal solvents, water and the like.

The starting materials and the intermediates of a reaction may be isolated and purified if desired using conventional techniques, including but not limited to filtration, distillation, crystallization, chromatography and the like. Such materials can be characterized using conventional means, including physical constants and spectral data.

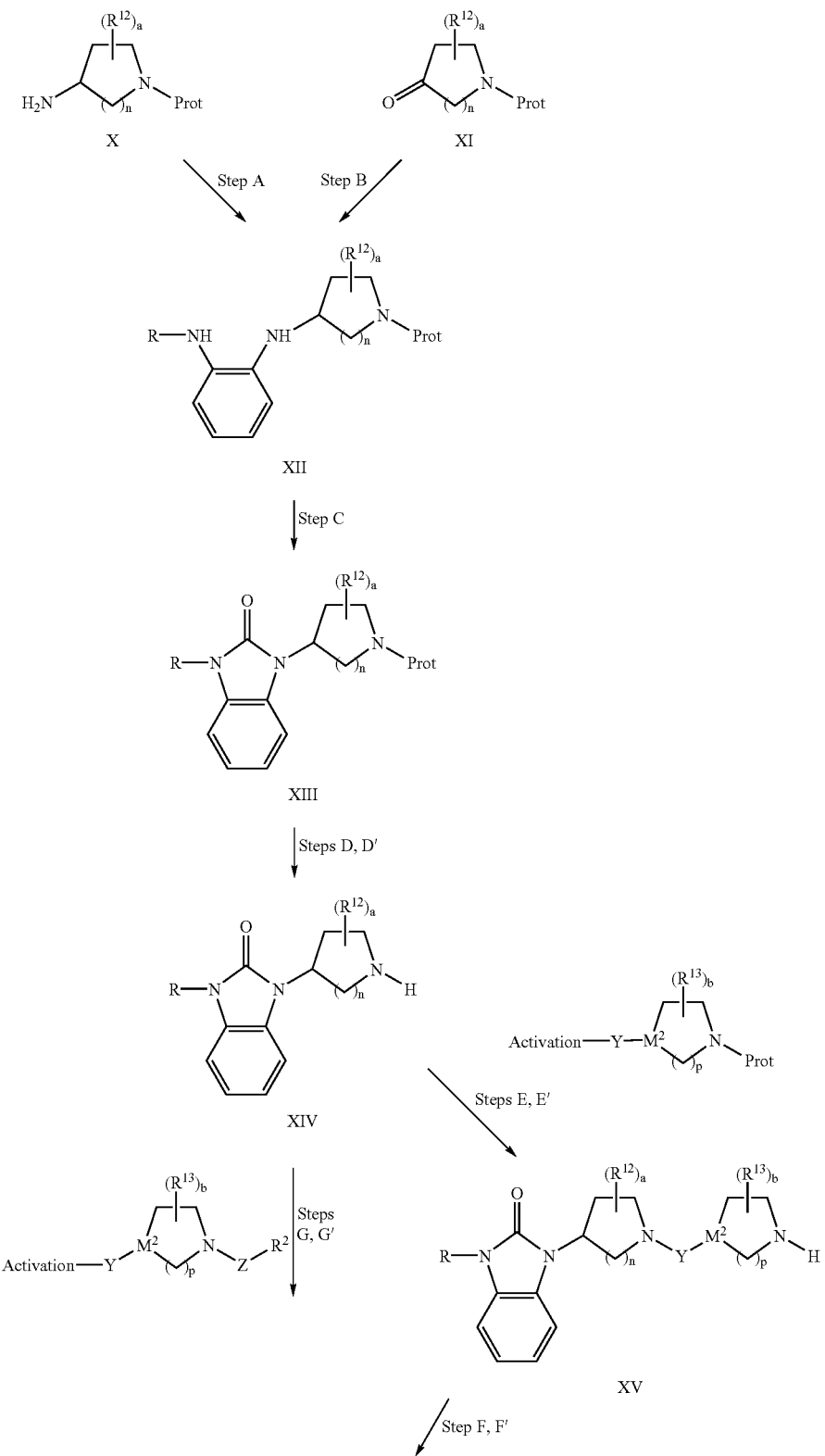
SCHEME 1
General Method for Preparation of Compounds of Formula XVI

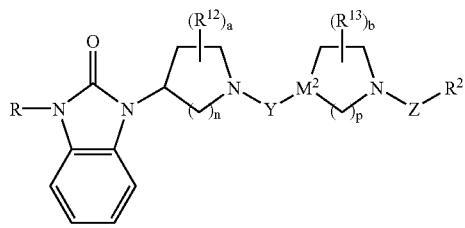

XVI (Steps D', E', F', G' are optional)

Step A: A suitably mono-protected amine of formula X is alkylated with a halide to form a compound of formula XII. A suitable halide for alkylation is a substituted 2-bromo nitrobenzene as described by Henning et al, *J. Med. Chem.* 30, (1987) 814. Suitable amine protecting groups are methyl, benzyl, ethoxycarbonyl or the like.

Step B: A suitably protected ketone of formula XI is reductively alkylated with an amine to form a compound of formula XII. Suitable amine protecting groups are methyl, benzyl, ethoxycarbonyl or the like.

Step C: An intermediate diamine of formula XII is then cyclized with an appropriate carbonyl equivalent such as phosgene, triphosgene or carbonyl diimidazole (CDI) to form a compound of formula XIII. Methods for cyclization have been described by Henning et al, *J. Med. Chem.* 30, (1987) 814.

Steps D & D': The protected amine of formula XIII is deprotected using methods known to those skilled in the art. See, for example, Green et al, *Protective Groups in Organic Synthesis*. A suitable method for methyl deprotection is reaction with a haloformate or the like. A suitable method for benzyl deprotection is cleavage with hydrogen at or above atmospheric pressure and a catalyst such as palladium. A suitable method for carbamate deprotection is treatment with an acid such as HCl.

Optionally, when R is H in formula XIII, derivatization can be accomplished before other steps by methods known to those skilled in the art. Preferred methods include, but are not limited to, alkylation with a halide under phase transfer conditions (e.g. biphasic basic conditions) or arylation with an aryl or heteroarylboronic acid under metal catalyzed conditions.

Steps E & E': An amine of formula XIV is reacted with an activated functional group to form the bond between the nitrogen and functional group Y in formula XV. When Y is a carbonyl group and $M^2$ is carbon, activation can be via a halide (i.e. acid chloride intermediate) and suitable reaction conditions may require a base such as triethylamine. When Y is a methylene and $M^2$ is a carbon, activation can be via a halide (i.e. iodomethyl intermediate) or an acid chloride as above followed by treatment with a reducing agent such as LAH. When Y is a sulfonyl and $M^2$ is a carbon, activation can be via a sulfonyl halide (i.e. sulfonyl chloride intermediate).

Optionally, when R is H in formula XIV, derivatization can be accomplished before other steps by methods known to those skilled in the art.

Steps F & F': The protected amine of formula XV is deprotected using methods known to those skilled in the art. A suitable method for methyl deprotection is reaction with a haloformate or the like. A suitable method for benzyl deprotection is cleavage with hydrogen at or above atmospheric pressure and a catalyst such as palladium. A suitable method for carbamate deprotection is treatment with an acid such as hydrochloric acid. The deprotected amine intermediate formed above is then alkylated with a suitable reagent such as halide-Z—$R^2$ to form the bond between nitrogen and Z in compound XVI.

Optionally, when R is H in formula XV, derivatization can be accomplished before other steps by methods known to those skilled in the art.

Steps G & G': An amine of formula XIV is reacted with an activated functional group to form the bond between the nitrogen and functional group Y in formula XV. When Y is a carbonyl group and $M^2$ is carbon, activation can be via a halide (i.e. acid chloride intermediate) and suitable reaction conditions may require a base such as triethylamine. When Y is a methylene and $M^2$ is a carbon, activation can be via a halide (i.e. iodomethyl intermediate) or an acid chloride as above followed by treatment with a reducing agent such as LAH. When Y is a sulfonyl and $M^2$ is a carbon, activation can be via a sulfonylhalide (i.e. sulfonyl chloride intermediate).

Optionally, when R is H in formula XIV, derivatization can be accomplished before other steps by methods known to those skilled in the art.

The preparation of intermediates of formula XIII is further elaborated in the following Schemes 2 and 3. Preparation of benzimidazoles is shown, but aza and diaza derivatives can be similarly prepared.

SCHEME 2
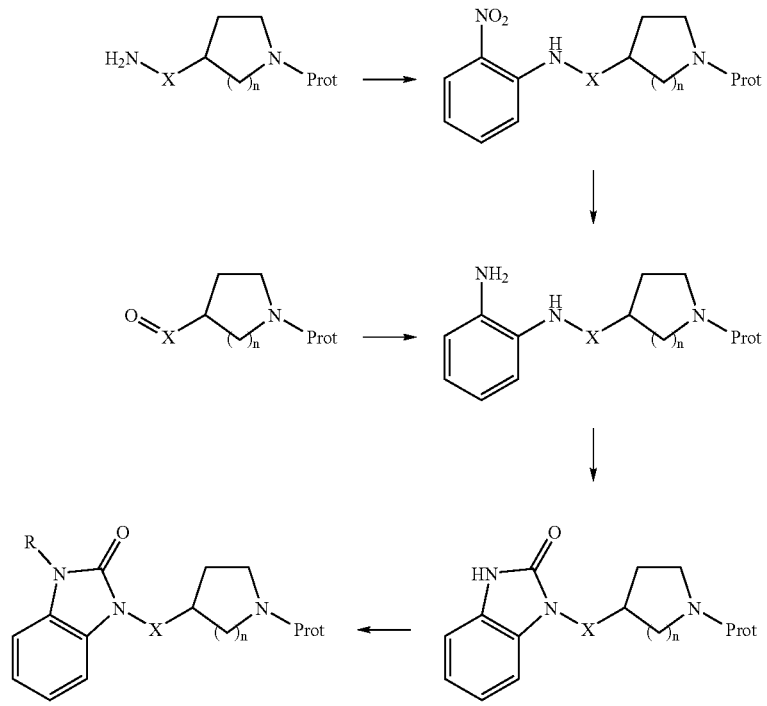
These procedures are described by Henning et al and in *J. Med. Chem.*, 41 (1998), p. 74.
This procedure is described in *J. Heterocyclic Chem.*, 20 (1983), p. 565.
SCHEME 3
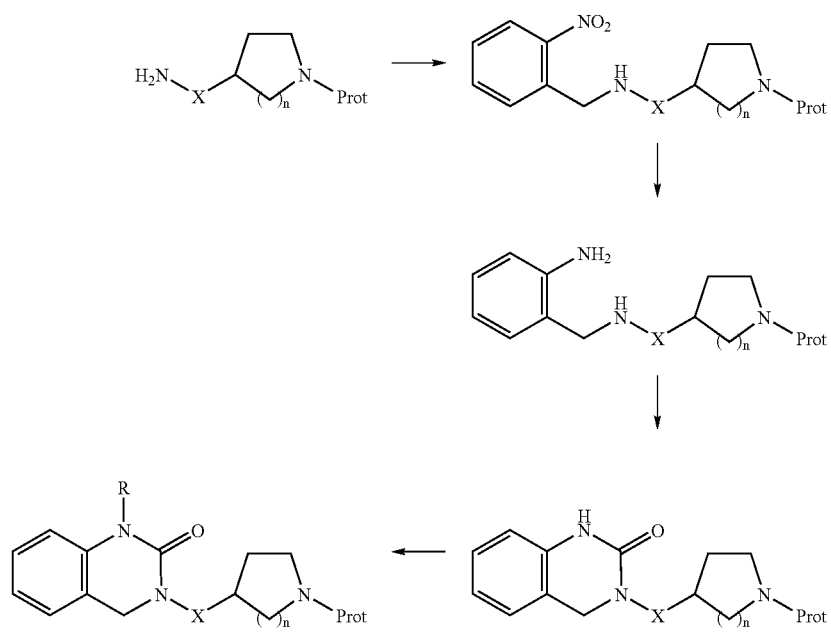

Compounds of formula I can be prepared by the general methods outlined in Schemes 1–3. Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

Unless otherwise stated, the following abbreviations have the stated meanings in the Examples below:
Me=methyl; Et=ethyl; Bu=butyl; Pr=propyl; Ph=phenyl; t-BOC=tert-butoxycarbonyl;
CBZ=carbobenzyloxy; and Ac=acetyl
DCC=dicyclohexylcarbodiimide
DMAP=4-dimethylaminopyridine
DMF=dimethylformamide
EDCl=1-(3-dimethylaminopropyl)-3-ethylcarbodiimide
HATU=O-(7-Azabenzotriazol-1-yl)-N,N,N',N'-tetramethyluronium hexafluorophosphate
HOBT=1-hydroxybenzotriazole
LAH=lithium aluminum hydride
NaBH(OAc)$_3$=sodium triacetoxyborohydride
NBS=N-bromosuccinimide
TBAF=tetrabutylammonium fluoride
TBDMS=t-butyldimethylsilyl
TMEDA=N,N,N',N'-tetramethylethylenediamine
TEMPO=2,2,6,6-tetramethyl-1-piperidinyloxy, free radical
TLC=thin layer chromatography
HRMS=High Resolution Mass Spectrometry
LRMS=Low Resolution Mass Spectrometry
nM=nanomolar
Ki=Dissociation Constant for substrate/receptor complex
pA2=−logEC$_{50}$, as defined by J. Hey, *Eur. J. Pharmacol.*, (1995), Vol. 294, 329–335.
Ci/mmol=Curie/mmol (a measure of specific activity)

Preparation 1

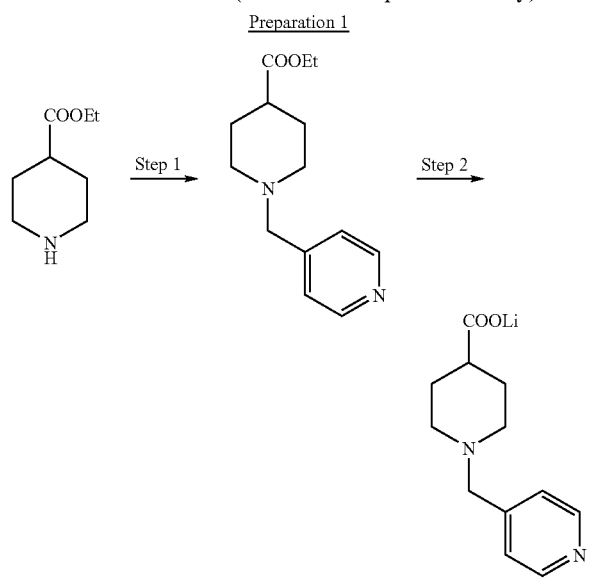

Step 1: To a solution of ethyl isonipecotate (147 g, 0.93 mol) in dichloroethane (1300 ml) was added 4-pyridinecarboxaldehyde (50.0 g, 0.47 mol) and crushed 3 Å molecular sieves (35 g). After 10 min., NaBH(OAc)$_3$ (198 g, 0.93 mol) was added, portionwise, and the reaction stirred at 23° C. After 16 h, water (300 ml) was slowly added, the organic layer separated, and the aqueous layer extracted with CH$_2$Cl$_2$. The combined organic extracts were dried (MgSO$_4$), filtered, and concentrated. The crude product was distilled under vacuum to afford 101.5 g (0.409 mol, 91%) of the desired compound as an oil (bp 148–150° C. @ 3 mm Hg). MS (ES) m/e 249 (MH$^+$).

Step 2: To a solution of the product of Step 1 (101.5 g, 0.409 mol) in CH$_3$OH (1000 ml) was added LiOH monohydrate in H$_2$O (1.0 M, 860 ml, 0.86 mol). The reaction was heated at reflux for 16 h, then concentrated. The remaining water was removed azeotropically with EtOH (3×300 ml) to give 104.5 g (0.384 mol, 94%) of the compound of Preparation 1 with LiOH as a white solid. MS (ES): m/e 221 (MH$^+$).

Preparation 2

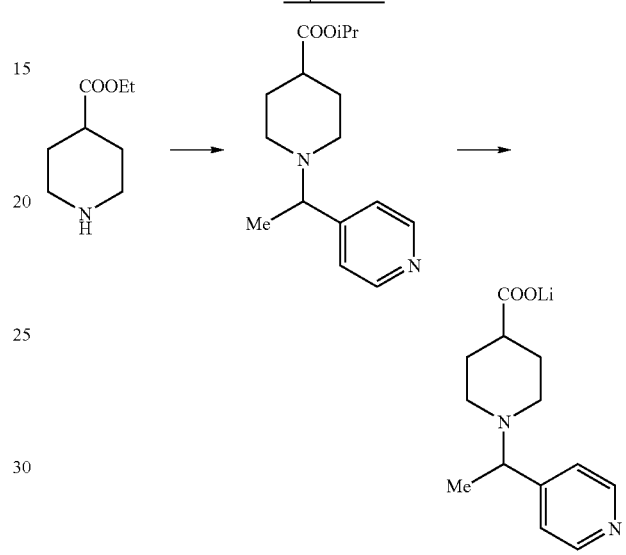

To a solution of ethyl isonipecotate (15.0 g, 95.4 mmol), was added 4-acetylpyridine (9.25 g, 76.3 mmol) and titanium isopropoxide (27.12 g, 95.4 mmol). The reaction was stirred at 23° C. for 16 h, and then EtOH (300 ml) and NaCNBH$_3$ (6.00 g, 95.4 mmol) were added. After an additional 24 h, water (300 ml) and CH$_2$Cl$_2$ (300 ml) were added. The reaction was filtered through celite and washed with water (300 ml) and CH$_2$Cl$_2$ (300 ml). The filtrate was transferred to a separatory funnel, 1 N NaOH was added and the organic layer separated. The combined organic extracts were dried (MgSO$_4$), filtered, and concentrated. Further purification by silica gel chromatography (eluant: 3% CH$_3$OH—CH$_2$Cl$_2$ then 6% CH$_3$OH—CH$_2$Cl$_2$) afforded 8 g (28.9 mol, 38% yield) of the desired compound as a yellow oil. MS (FAB for M+1): m/e 277. This compound was hydrolyzed with LiOH monohydrate as in Preparation 1 to afford the compound of Preparation 2.

The following compound was prepared according to the same above procedure:

Preparation 2A: MS (ES): m/e 291 (MH$^+$).

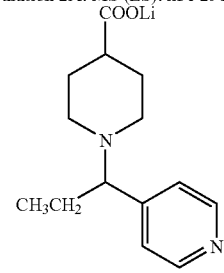

-continued

Preparation 3

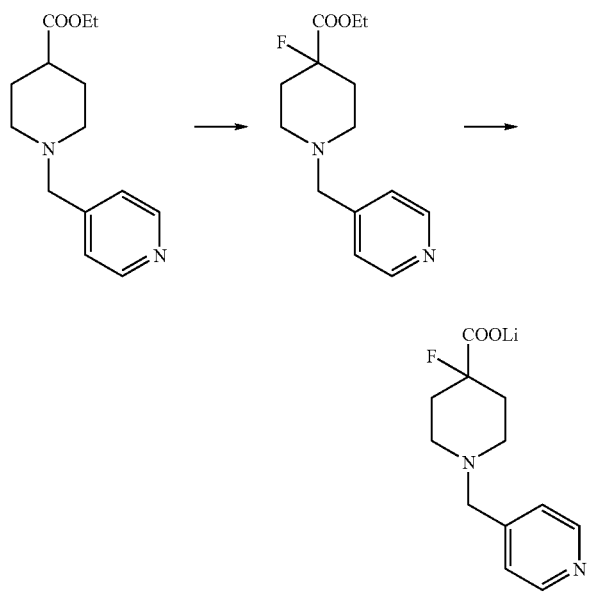

To a solution of diisopropylamine (2.28 g, 3.2 ml, 22.55 mmol) in dry THF (50 mL) at 0° C. under N₂ was added n-butyl lithium (2.5 M, 8.4 ml, 20.94 mmol) via syringe. After 10 min, the reaction was cooled to −78° C. and the product of Prearation 1, Step 1(4.00 g, 16.11 mmol) in dry THF (10 ml) was added dropwise via an addition funnel. After 3 h at −78° C., N-fluorobenzenesulfonimide (6.60 g, 20.94 mmol) was added, and the reaction was then allowed to warm slowly to 23° C. overnight. The reaction was quenched by addition of 0.5 N NaOH (100 ml) and extracted with EtOAc. The combined organic extracts were dried (MgSO₄), filtered, and concentrated. Purification by silica gel chromatography (eluant: 2% CH₃OH—CH₂Cl₂ then 3% CH₃OH—CH₂Cl₂) afforded 0.63 g (2.37 mmol, 15%) of the desired compound as a yellow oil. MS (FAB for M+1): m/e 267. This compound was hydrolyzed with LiOH monohydrate as in Preparation 1 to afford the compound of Preparation 3.

Preparation 4

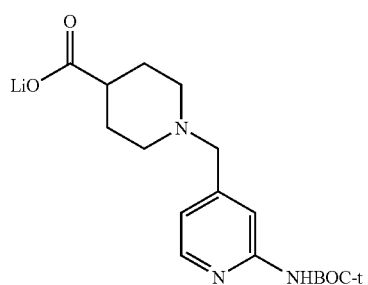

Step 1:

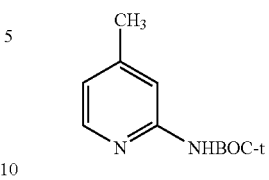

To a solution of 2-amino-4-methylpyridine (10.81 g, 100 mmol) in tert-butanol (250 ml) was added t-BOC anhydride (26.19 g, 120 mmol). The reaction mixture was stirred at 23° C. overnight, and then concentrated to an oil. The crude product was dry loaded onto a silica gel column and flash chromatographed (eluant: 30% hexanes-CH₂Cl₂ to 0–2% acetone-CH₂Cl₂) to obtain 15.25 g (73.32 mmol; 73%) of the desired product as a white solid.

Step 2:

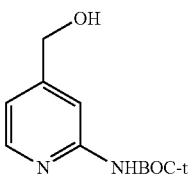

To a solution of the product of Step 1 (35.96 g, 173 mmol) in THF (1.4 l) at −78° C. was added n-BuLi (1.4 M, 272 ml, 381 mmol) in hexanes portionwise over 30 min. The reaction mixture was then allowed to warm slowly and was stirred for 2 h at 23° C., which resulted in the formation of an orange precipitate. The mixture was then recooled to −78° C., and pre-dried oxygen (passed through a Drierite column) was bubbled through the suspension for 6 h while the temperature was maintained at −78° C. The color of the reaction mixture changed from orange to yellow during this time. The reaction was quenched at −78° C. with (CH₃)₂S (51.4 ml, 700 mmol) followed by AcOH (22 ml, 384 mmol) and allowed to warm slowly to room temperature. After 48 h, water was added and the product extracted into EtOAc. Purification by silica gel flash chromatography (eluant: 0–15% acetone/CH₂Cl₂) provided 20.15 g (90 mmol; 52%) of the alcohol as a pale yellow solid.

Step 3:

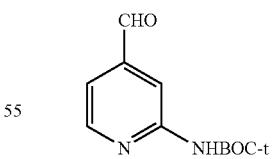

To a solution of the product of Step 2 (19.15 g, 85.5 mmol) in CH₂Cl₂ (640 ml) was added a saturated aqueous solution of NaHCO₃ (8.62 g, 103 mmol) and NaBr (444 mg, 4.3 mmol). The reaction mixture was cooled to 0° C., and TEMPO (140 mg, 0.90 mmol) was introduced. Upon vigorous stirring, commercial bleach solution (122 ml, 0.7 M, 85.4 mmol) (5.25% in NaOCl) was added portionwise over 40 min. After an additional 20 min at 0° C., the reaction mixture was quenched with saturated aqueous Na₂S₂O₃ and allowed to warm to 23° C. Dilution with water and extraction with CH$_2$Cl$_2$, followed by concentration and flash chromatography (eluant: 30% hexanes-CH$_2$Cl$_2$ to 0–2% acetone-CH$_2$Cl$_2$) afforded 15.97 g (71.9 mmol; 84% yield) of the aldehyde as an off-white solid.

Step 4:

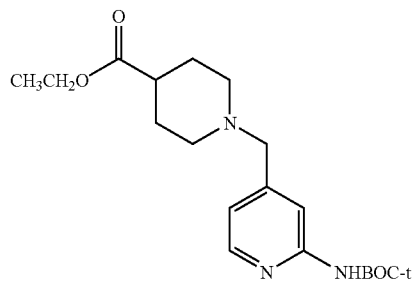

To a solution of the product of Step 3 (11.87 g, 53.5 mmol) in CH$_2$Cl$_2$ (370 ml) was added ethyl isonipecotate (9.07 ml, 58.8 mmol) followed by four drops of AcOH. The reaction mixture was then stirred for 40 min at 23° C., after which NaB(OAc)$_3$H (22.68 g, 107 mmol) was added. The reaction mixture was stirred overnight at 23° C., neutralized with saturated aqueous NaHCO$_3$, diluted with water and extracted with CH$_2$Cl$_2$. Concentration of the organic extracts, followed by silica gel flash chromatography (eluant: 0–4% sat. NH$_3$ in CH$_3$OH—CH$_2$Cl$_2$) provided 19.09 g (52.6 mmol; 98%) of the ester as an off-white solid.

Step 5:

To a solution of the product of Step 5 (1.57 g, 4.33 mmol) in THF-water-CH$_3$OH (10 ml of a 3:1:1 mixture) was added LiOH monohydrate (0.125 g, 5.21 mmol). The reaction mixture was stirred overnight at 23° C., concentrated and dried under high vacuum to obtain 1.59 g of crude title compound as a yellowish solid which was used without purification.

Preparation 5

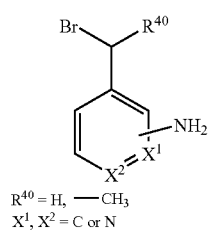

R$^{40}$ = H, —CH$_3$
X$^1$, X$^2$ = C or N

Step 1:

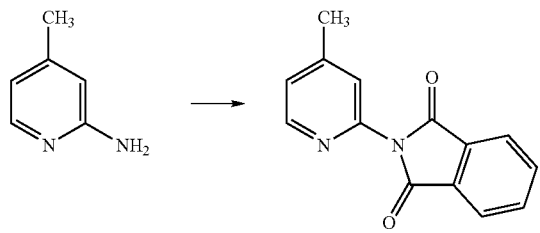

To a solution of the substituted pyridine (30 g, 277 mmol) and DMAP (100 mg, 0.82 mmol) in CH$_2$Cl$_2$ (800 ml) was added a solution of phthaloyl dichloride (56.3 g, 277 mmol) in CH$_2$Cl$_2$ (70 ml) via an addition funnel. The reaction mixture was stirred at 23° C. for 2 h, and then aqueous NaHCO$_3$ was added slowly. The organic layer was separated, and the aqueous layer further extracted with CH$_2$Cl$_2$. The combined organic layers were washed with water, dried, and concentrated to provide the desired compound as an off-white solid (61.2 g, 92%). MS (Cl): 239 (MH$^+$)

The following compounds were prepared using a similar procedure and the appropriate starting materials:

| | Compounds | MS (Cl) |
|---|---|---|
| 5-1A | 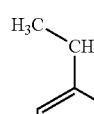 | 253 (MH$^+$) |
| 5-1B | 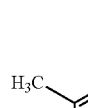 | 239 (MH$^+$) |

A suspension of the compound of Step 1 (10.94 g, 45.92 mmol), NBS (25 g, 140.5 mmol) and benzoyl peroxide (1.15 g, 4.75 mmol) in CCl$_4$ (300 ml) was refluxed for 20 h, cooled to 23° C., and filtered. The filtrate was concentrated. The resulting crude product was purified by silica gel flash chromatography (eluant: 40% EtOAc-hexanes) to give a tan solid (5.20 g). $^1$H NMR revealed this was a mixture of the starting material and product with a ratio 1.4:1. The calculated yield is 15%. MS (Cl): 317 (M+1).

The following compounds were prepared using a similar procedure and the appropriate starting materials:

| | Compounds | MS (Cl) |
|---|---|---|
| 5-2A | 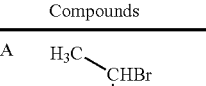 | — |

-continued

| Compounds | | MS (Cl) |
|---|---|---|
| 5-2B | 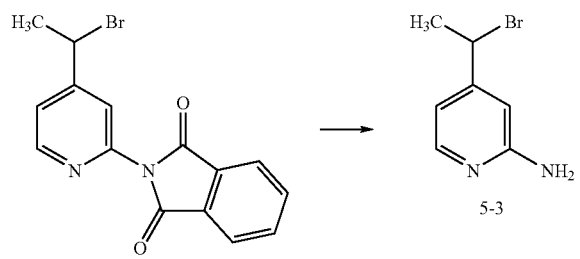 | 317 (MH+) |
| 5-2C | | 250 (MH+) |

Step 3:

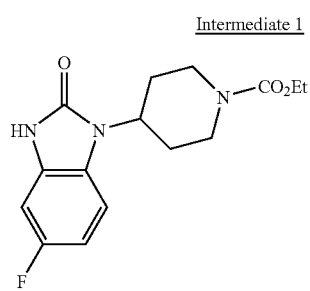

To a solution of Preparation 5-2A (4.5 g, 13.6 mmol) in EtOH (55 ml) was added hydrazine (0.48 g, 14.9 mmol). The reaction mixture was stirred at 23° C. for 2 h, concentrated, treated with water and $CH_2Cl_2$. The organic layer was separated, dried, and concentrated. Silica gel flash chromatography of the crude product (eluant: 2% $CH_3OH$—$CH_2Cl_2$) provided the desired compound as a white solid. (1.0 g, 37%).

Preparation 6

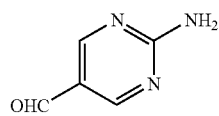

The compound is prepared according to the procedure described in JP Patent 63227573, 1988.

Intermediate 1

-continued (Steps A and C of Scheme 1)

Step A:

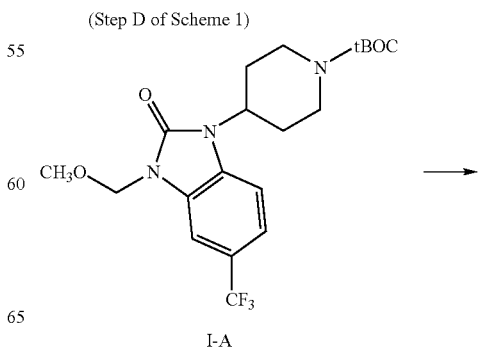

2-Chloro-5-fluoro nitrobenzene (40 g, 225 mmol), ethyl 4-amino-1-piperidinecarboxylate (39 g, 226 mmol), $K_2CO_3$ (65 g, 470 mmol) were combined and heated to 150° C. After 16 h the reaction was cooled, diluted with $CH_2Cl_2$, washed with water and the organic layer concentrated to a brown semi-solid. Further purification by silica gel chromatography (20:80 EtOAc:hexanes) afforded the nitro-aromatic intermediate (42 g, 60% yield, m/e 311).

The nitro-aromatic intermediate (10 g, 32 mmol) was dissolved in a mixture of ethanol (36 ml) and THF (72 ml) in a Parr pressure vessel. Raney Nickel (~3.3 g wet) was added and the reaction was shaken under $H_2$ at 40 psi for 2 h. TLC (1:1 EtOAc:hexanes) indicated reaction was complete. The reaction mixture was filtered through celite and the filtrate concentrated to afford the desired product (8.6 g, 96% yield, m/e 281).

Step C:

The product of Step A (18 g, 64 mmol) was dissolved in $CH_2Cl_2$ (700 ml) and cooled to 0° C. Triphosgene (16 g, 54 mmol) was added slowly followed by $Et_3N$ (18 ml, 245 mmol). The reaction was allowed to warm slowly to 23° C. over 3 h. The reaction was washed with 1 N HCl, then water. The organic layer was dried over $Na_2SO_4$ to afford the product as an off-white solid (11.2 g, 60% yield, m/e 307).

Intermediate 2

(Step D of Scheme 1)

I-A

-continued

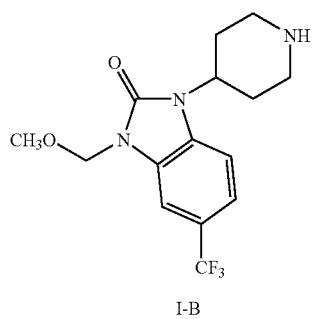

I-B

To a suspension of anhydrous $ZnBr_2$ (1.0 g, 4.4 mmol) in $CH_2Cl_2$ (15 ml) was added a solution of compound I-A (432 mg, 1.0 mmol) in $CH_2Cl_2$ (15 ml) and the reaction was stirred at 23° C. for 16 h. Saturated $NaHCO_3$ and 1 N NaOH solution were added, and the product extracted with $CH_2Cl_2$. The combined organic extracts were washed with brine, dried ($Na_2SO_4$), filtered, and concentrated. Purification by silica gel chromatography (eluant: 1:1 $CH_2Cl_2$:4% $NH_3$ in $CH_3OH$) afforded 0.22 g (0.67 mmol, 67%) of I-B as a white solid. MS: m/e 330 ($MH^+$)

Intermediate 3

(Steps D' and D of Scheme 1)

Step D':

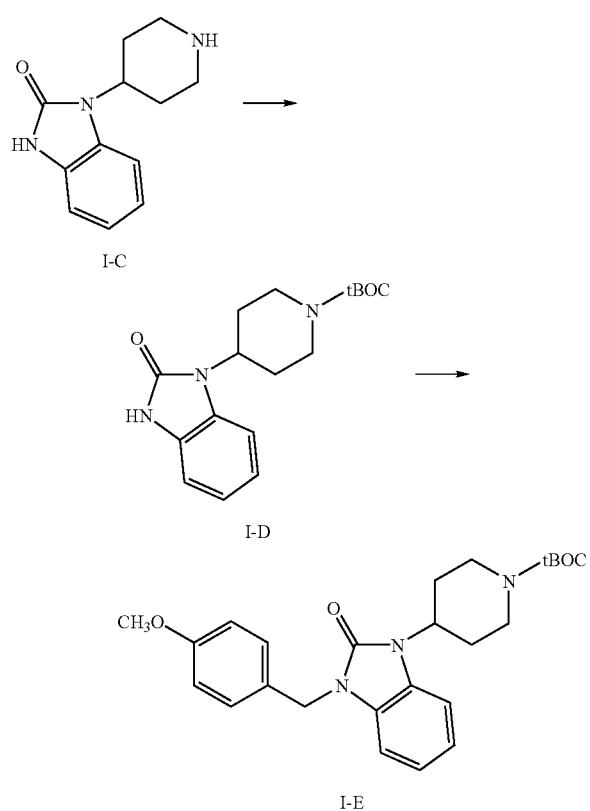

To a solution of I-C (10.19 g, 46.9 mmol) in 1,2-dichloroethane (200 ml) was added di-t-butyl dicarbonate (10.24 g, 47 mmol). The reaction was heated at reflux for 20 min. and then stirred at 23° C. for 1 h. The solvent was evaporated to give 14.89 g (46.9 mmol, 100% yield) of the N-Boc protected intermediate, I-D, as a white foam. MS (FAB for M+1): m/e 318.

To a solution of I-D (1.0 g, 3.15 mmol) in toluene (20 ml) was added NaOH (0.44 g, 11.0 mmol), $K_2CO_3$ (0.87 g, 6.30 mmol), tetra-n-butylammonium sulfate (0.21 g, 0.63 mmol) and 4-methoxybenzyl chloride (0.74 g, 4.73 mmol). The reaction was heated at reflux for 16 h and then cooled to 23° C. Water (30 ml) was added, and the crude product isolated by extraction with EtOAc. The combined organic extracts were dried ($MgSO_4$), filtered, and concentrated. Purification by silica gel chromatography (eluant: 3% $CH_3OH$—$CH_2Cl_2$) gave 1.26 g (2.88 mmol, 91%) of I-E as a white foam. MS (FAB for M+1): m/e 438.

Step D:

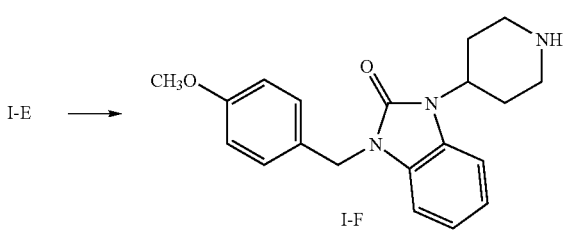

To a solution of compound I-E (1.25 g, 2.86 mmol) in $CH_2Cl_2$ (20 ml) was added HCl in dioxane (4 N, 2.9 ml, 11.4 mmol). The reaction was stirred for 16 h at 23° C., concentrated, 1 N NaOH (30 ml) was added, and the product extracted with $CH_2Cl_2$. The combined organic extracts were dried ($MgSO_4$), filtered, and concentrated to give 0.96 g (2.86 mmol, 100%) of I-F as a colorless oil. MS (FAB for M+1): m/e 338.

Other R-substituted benzimidazolone derivatives were made in a similar manner.

Intermediate 4

(Step D' of Scheme 1)

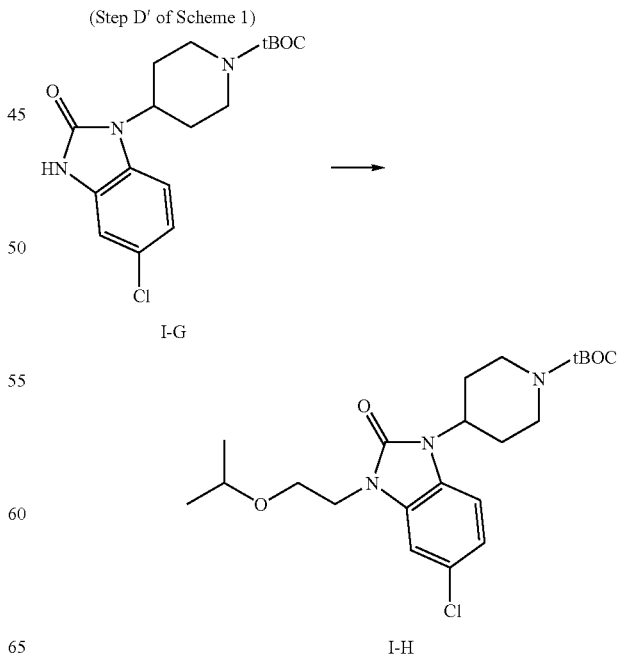

To a solution of I-G (1.0 g, 2.84 mmol) in DMF (20 ml) was added NaH (60 wt %, 0.082 g, 3.41 mmol). After 1 h at 23° C. excess methylsulfonyloxyethylisopropyl ether was added, and the reaction was then heated to 100° C. After 16 h, the reaction was cooled, water (50 ml) was added and the product extracted with CH₂Cl₂. The combined organic extracts were dried (MgSO₄), filtered, and concentrated. Purification by silica gel chromatography (eluant: 20% EtOAc-CH₂Cl₂) afforded 1.20 g (2.74 mmol, 100% yield) of I-H as a foam. MS (ES for M+1): m/e 438.

Intermediate 5

(Step D' of Scheme 1)

I-D ⟶

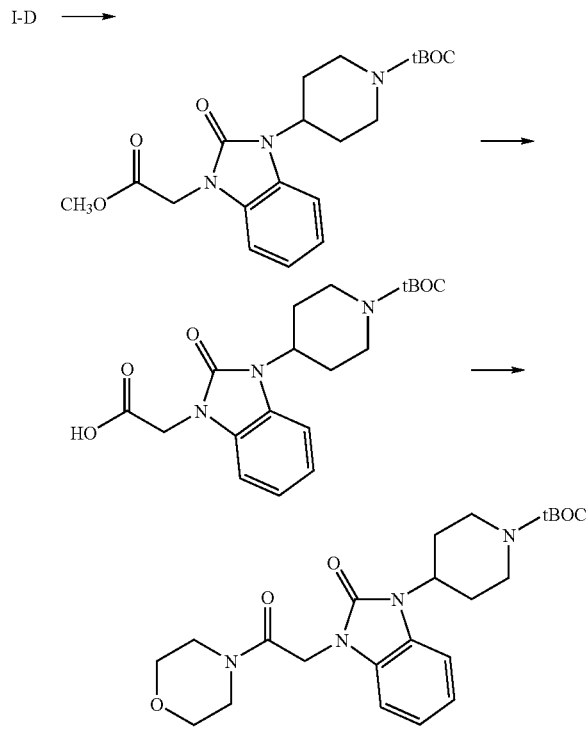

To a solution of I-D (4.0 g, 12.7 mmol) in dry DMF (40 ml) at −78° C. was added lithium bis(trimethylsilyl)amide (1.0 M in THF, 16.5 ml, 16.5 mmol) dropwise via syringe. The reaction was stirred at −78° C. for 60 min., methyl bromoacetate (2.90 g, 1.8 ml, 19.0 mmol) was then added and the reaction warmed slowly to 23° C. After 16 h the solvent was evaporated, saturated NH₄Cl (60 ml) added, and the product extracted with EtOAc. The combined organic extracts were dried (MgSO₄), filtered, and concentrated. Purification by silica gel chromatography (eluant: 40% EtOAc-hexane) afforded 3.37 g (8.66 mmol, 69%) of I-I as a white foam. MS (Cl for M+1): m/e 390.

To a solution of I-I (3.36 g, 8.66 mmol) in 1:1 CH₃OH: H₂O by volume (50 ml) was added LiOH.H₂O (0.76 g, 17.3 mmol) and the reaction was heated to reflux for 3 h. The reaction was cooled and the solvent evaporated to give 3.49 g (8.62 mmol, 99%) of I-J (with 1 equivalent of LiOH) as a white solid. MS (FAB for M+1): m/e 382.

To a solution of compound I-J (1.64 g, 4.30 mmol) in 1:1 CH₂Cl₂:DMF by volume (40 ml) was added HOBT (0.88 g, 6.50 mmol), EDCl (1.25 g, 6.50 mmol), and morpholine (0.49 g, 5.60 mmol). After 0.5 h the reaction was heated to reflux for 16 h. The reaction was cooled, concentrated, 0.5 N NaOH (30 ml) was then added, and the product extracted with CH₂Cl₂. The combined organic extracts were dried (MgSO₄), filtered, and concentrated. Purification by silica gel chromatography (eluant: 5% CH₃OH—CH₂Cl₂) gave 1.91 g (4.30 mmol, 100%) of I-K as an oil. MS (ES for M+1): m/e 445.

Intermediate 6

(Step E of Scheme 1)

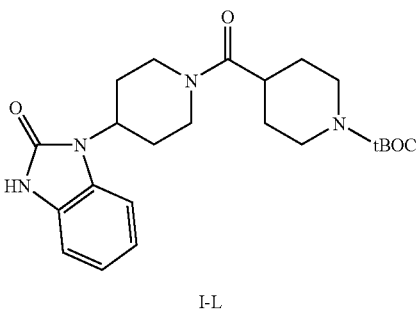

I-L

To a solution of I-C (4.52 g, 20.8 mmol) in CH₂Cl₂ (100 ml) was added t-BOC-isonipecotic acid (5.25 g, 22.9 mmol), DCC (5.37 g, 26.0 mmol), and HOBT (3.51 g, 26.0 mmol) and the reaction stirred at 23° C. for 16 h. The solids were filtered, and the filtrate transferred to a separatory funnel. 0.5 N NaOH (200 ml) was added, and the product extracted with CH₂Cl₂. The combined organic extracts were dried (MgSO₄), filtered, and concentrated. Purification by silica gel chromatography (eluant: 5% CH₃OH—CH₂Cl₂, then 8% CH₃OH—CH₂Cl₂) afforded 8.51 g (19.9 mmol, 95% yield) of I-L as a white foam. MS (ES for M+1): m/e 429.

The following compounds were prepared using a similar procedure and the appropriate starting materials:

| Compound | | MS (Cl, FAB, or ES) |
|---|---|---|
| 1-M | (structure) | 443 (MH⁺) |
| 1-N | (structure) | 497 (MH⁺) |

Intermediate 7
(Step E of Scheme 1)

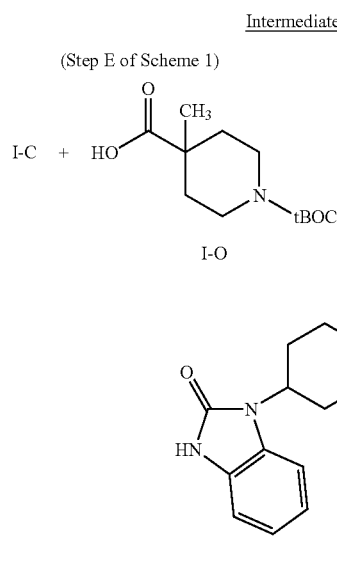

To a mixture of Intermediate I-C (4.45 g, 20.48 mmol), I-O (5.00 g, 20.55 mmol), and DMAP (5.10 g, 41.75 mmol) in DMF (200 ml) was added HATU (7.90 g, 20.78 mmol). The resulting solution was stirred at 23° C. for 16 h, and quenched with cold water (250 ml). The reaction mixture was transferred to separatory funnel, and the product extracted with ether. The combined organic layers were washed with saturated brine (2×200 ml), dried over MgSO$_4$, and concentrated. Purification by silica chromatography (10% CH$_3$OH in CH$_2$Cl$_2$) gave a yellow gel, which was crystallized from ether to provide a white solid (6.93 g). The mother liquid was concentrated and recrystallization from 100 ml of ether delivered another portion of white solid (0.20 g). Combined yield of I-P was 79%.

Intermediate 8
(Step E' of Scheme 1)

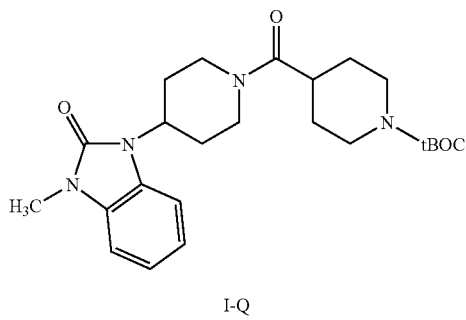

I-Q

To a solution of I-L (1.00 g, 2.33 mmol) in toluene (20 ml) was added NaOH (0.33 g, 8.17 mmol), K$_2$CO$_3$ (0.64 g, 4.67 mmol), tetrabutylammonium hydrogensulfate (0.16 g, 0.467 mmol), and dimethylsulfate (0.44 g, 0.33 ml, 3.50 mmol). The reaction was heated at reflux for 16 h then cooled. Water (40 ml) was added, and the product extracted with EtOAc. The combined organic extracts were dried (MgSO$_4$), filtered, and concentrated. Purification by silica gel chromatography (eluant: 5% CH$_3$OH—CH$_2$Cl$_2$) gave 0.99 g (2.24 mmol, 96%) of I-Q as a white foam. MS (ES for M+1): m/e 443.

The following compounds were prepared according to the same above procedure:

| Compound | | MS (Cl, FAB, or ES) |
|---|---|---|
| I-R | (structure) | 485 (MH$^+$) |
| I-S | (structure) | 519 (MH$^+$) |

Intermediate 9

(Step F' of Scheme 1)

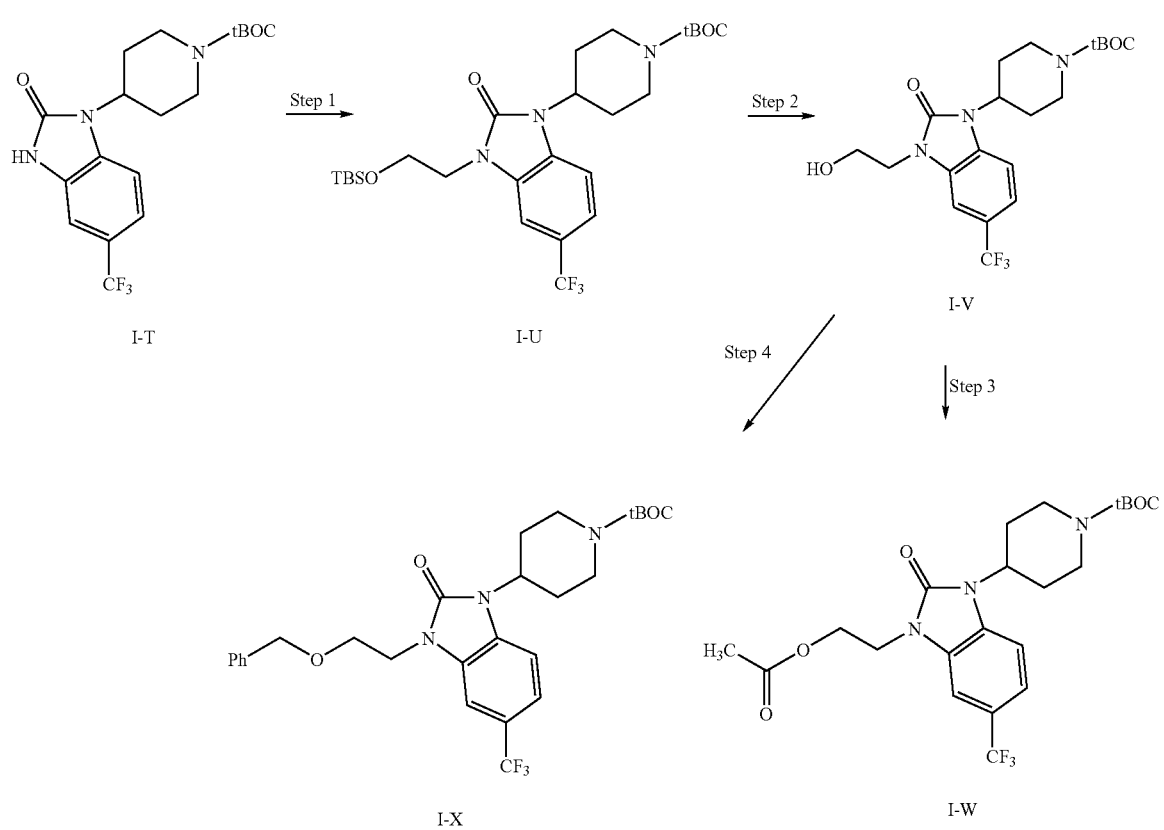

Step 1: To a solution of I-T (1.42 g, 2.86 mmol) in dry DMF (7.2 ml) was added 60% NaH (458 mg, 11.4 mmol) portionwise. After 10 min, 2-bromoethyl t-butyldimethylsilyl ether (1.23 ml, 5.7 mmol) was added and the reaction stirred for 15 h at 23° C., then heated at 45° C. for 7 h. The reaction was quenched by slow addition into cold $NH_4Cl$ solution and the product extracted with EtOAc. The combined organic extracts were washed with brine, dried ($Na_2SO_4$), filtered, and concentrated. Purification by silica gel chromatography (eluant: EtOAc) afforded 1.0 g (1.53 mmol, 53%) of product I-U as a white solid. MS: m/e 655 ($MH^+$).

Step 2: To a solution of I-U (1.0 g, 1.53 mmol) in THF (7.6 ml) was added TBAF (3.1 ml, 3.1 mmol, 1 M in THF) and the reaction stirred at 23° C. After 2.5 h, EtOAc was added and the organic layer washed with brine. The organic layer was dried ($Na_2SO_4$), filtered, and concentrated to give 0.67 g (1.25 mmol, 82%) of the product I-V as a white solid. MS: m/e 541 ($MH^+$).

Step 3: To a solution of I-V (250 mg, 0.46 mmol) in $CH_2Cl_2$ (3.2 ml) at 0° C. was added $Et_3N$ (97 μl, 0.69 mmol), DMAP (68 mg, 0.55 mmol), and $Ac_2O$ (65 μl, 0.69 mmol). The reaction was allowed to warm to 23° C. After 2 h, saturated $NaHCO_3$ solution was added and the product extracted with EtOAc. The combined organic extracts were washed with brine, dried ($Na_2SO_4$), filtered, and concentrated. Purification by silica gel chromatography (eluant: EtOAc) afforded 0.173 g (0.30 mmol, 64% yield) of I-W as a white solid. MS: m/e 583 ($MH^+$).

The following compound was prepared according to the same above procedure:

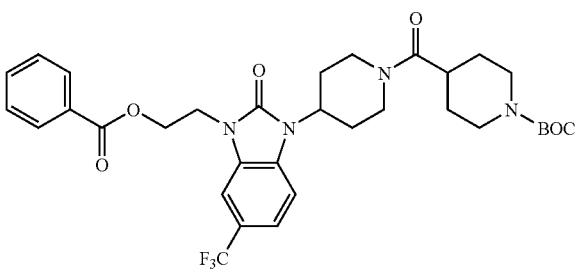

I-Y: MS: m/e 645 ($MH^+$)

Step 4: To a solution of I-V (173 mg, 0.32 mmol) in dry THF (3.2 ml) was added 60 wt % NaH (38 mg, 0.96 mmol) portionwise at 23° C. After 10 min., benzylbromide (144 μl, 0.96 mmol) was added. After 3.5 h, the reaction was poured slowly into cold $NH_4Cl$ solution and extracted with EtOAc. The combined organic extracts were washed with brine, dried ($Na_2SO_4$), filtered, and concentrated. Purification by silica gel chromatography (eluant: EtOAc) afforded 0.166 g (0.26 mmol, 82% yield) of I-X as a white solid. MS: m/e 631 ($MH^+$).

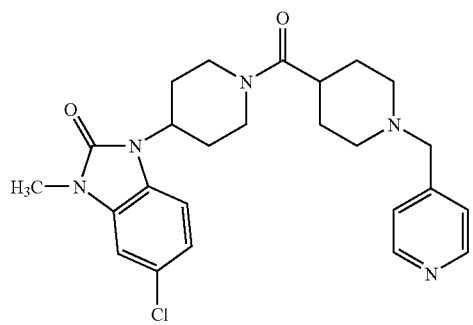

Step D':

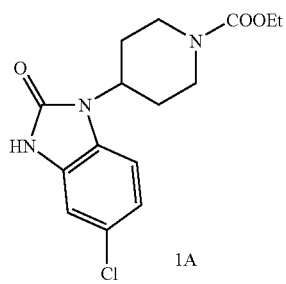
1A

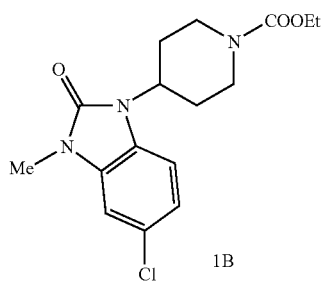
1B

To a suspension of compound 1A (0.3 g, 4.02 mmol) in dry toluene (30 ml), was added NaOH (0.56 g, 14.05 mmol), $K_2CO_3$ (1.11 g, 8.00 mmol), tetra-n-butylammonium sulfate (0.27 g, 0.80 mmol) and dimethylsulfate (0.76 g, 0.57 ml, 6.02 mmol). The reaction was refluxed for 16 h and then cooled to 23° C. The solvent was evaporated, water added (50 ml), and the product extracted with $CH_2Cl_2$. The combined organic extracts were dried ($MgSO_4$), filtered, and concentrated to afford 1.0 g (2.96 mmol, 71% yield) of the product 1B as a cream solid (mp 138–139° C.). MS (Cl) m/e 338 (MH$^+$)

Step D:

1B ⟶

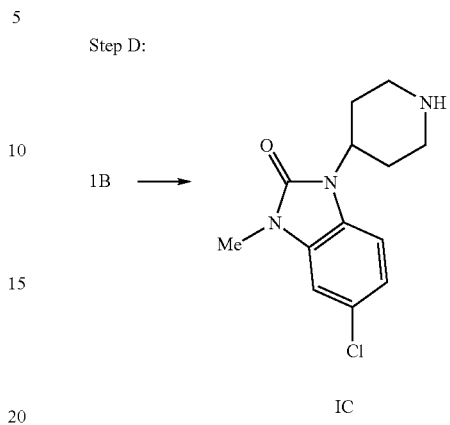
IC

To a solution of 1B (1.0 g, 2.96 mmol) in ethanol (75 ml) was added 25% NaOH in water (12 ml). The reaction was heated at reflux for 16 h and then cooled to 23° C. The solvent was evaporated, and the product partitioned between saturated NaCl and $CH_2Cl_2$. The combined organic extracts were dried ($MgSO_4$), filtered, and concentrated to give 0.77 g (2.90 mmol, 97%) of 1C as a white solid (mp 194–195° C.). MS (Cl) m/e 266 (MH$^+$).

Step G:

Compound 1C (0.50 g, 1.88 mmol) was dissolved in a 1:1 $CH_2Cl_2$:DMF (20 ml) mixture and HOBT (0.38 g, 2.82 mmol), EDCI (0.54 g, 2.82 mmol), and the product of Preparation 1 (0.53 g, 2.35 mmol) were added. After 0.5 h, the reaction was heated to reflux for 16 h. The reaction was then cooled, quenched with 0.5 N NaOH (30 ml) and extracted with $CH_2Cl_2$. The combined organic extracts were dried ($MgSO_4$), filtered, and concentrated. Purification by silica gel chromatography (eluant: 5% $CH_3OH$ with $NH_3$—$CH_2Cl_2$) gave 0.70 g (1.50 mmol, 80% yield) of Example 1 as a foam. MS (Cl) m/e 468 (MH$^+$).

The following compounds were prepared in a similar fashion.

| Compound | | MS(Cl, FAB, ES) |
|---|---|---|
| 1A | (structure) | 512 (MH$^+$) |

-continued
| Compound | MS(Cl, FAB, ES) |
|---|---|
| 1B 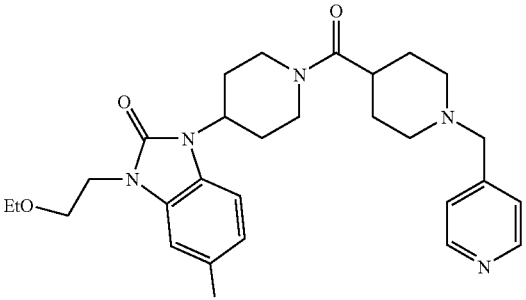 | 526 (MH⁺) |
| 1C 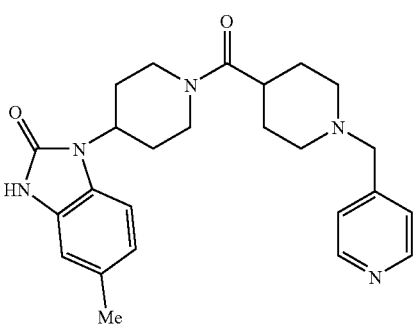 | 434 (MH⁺) |
| 1D 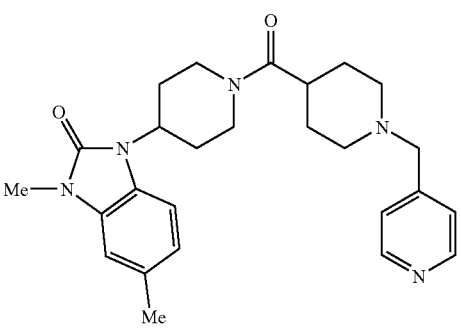 | 448 (MH⁺) |
| 1E 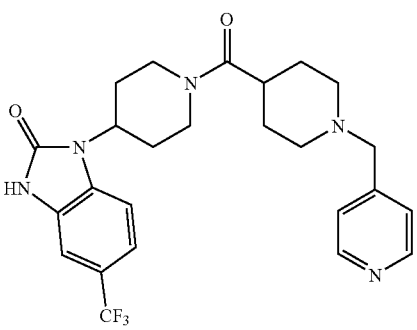 | 488 (MH⁺) |

-continued

| Compound | MS(Cl, FAB, ES) |
|---|---|
| 1F | 502 (MH⁻) |
| 1G | 578 (MH⁺) |
| 1H | 532 (MH⁺) |
| 1I | 546 (MH⁺) |

-continued

| Compound | MS(Cl, FAB, ES) |
|---|---|
| 1J | 532 (M−SiMe₂tBu+1) |
| 1K | 454 (MH⁺) |
| 1L | 468 (MH⁺) |
| 1M | 544 (MH⁺) |
| 1N | 488 (MH⁺) |

-continued
| Compound | MS(Cl, FAB, ES) |
|---|---|
| 1P 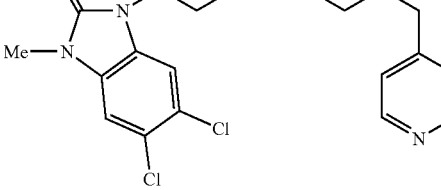 | 502 (MH+) |
| 1O 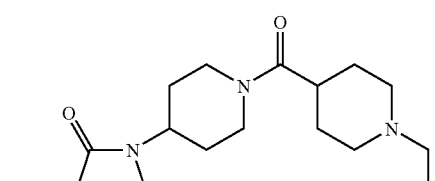 | 578 (MH+) |
| 1Q 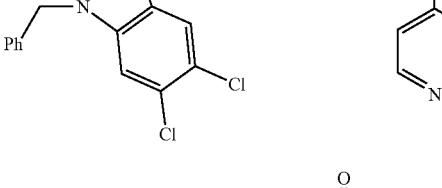 | 546 (MH+) |
| 1R 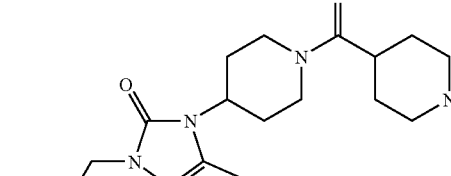 | 601 (MH+) |
| 1S 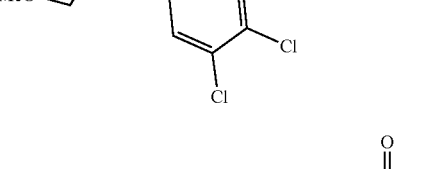 | 420 (MH+) |

-continued

| Compound | MS(Cl, FAB, ES) |
|---|---|
| 1T | 540 (MH+) |
| 1U | 540 (MH+) |
| 1V | 570 (MH+) |
| 1W | 544 (MH+) |

-continued

| Compound | MS(Cl, FAB, ES) |
|---|---|
| 1X | 544 (MH+) |
| 1Y | 464 (MH+) |
| 1z | 544 (MH+) |
| 1AA | 478 (MH+) |
| 1AB | 492 (MH+) |

-continued

| Compound | MS(Cl, FAB, ES) |
|---|---|
| 1AC | 506 (MH⁺) |
| 1AD | 506 (MH⁺) |
| 1AE | 540 (MH⁺) |
| 1AF | 522 (MH⁺) |
| 1AG | 491 (MH⁺) |

| Compound | | MS(Cl, FAB, ES) |
|---|---|---|
| 1AH | | 505 (MH$^+$) |
| 1AI | | 531 (MH$^+$) |
| 1AJ | | 533 (MH$^+$) |
| 1AK | | 517 (MH$^+$) |
| 1AL | | 513 (MH$^+$) |

-continued

| Compound | MS(CI, FAB, ES) |
|---|---|
| 1AM | 511 (MH+) |
| 1AN | 511 (MH+) |
| 1AO | 492 (MH+) |
| 1AP | 547 (MH+) |
| 1AQ | 540 (MH+) |

-continued
| Compound | | MS(Cl, FAB, ES) |
|---|---|---|
| 1AR | 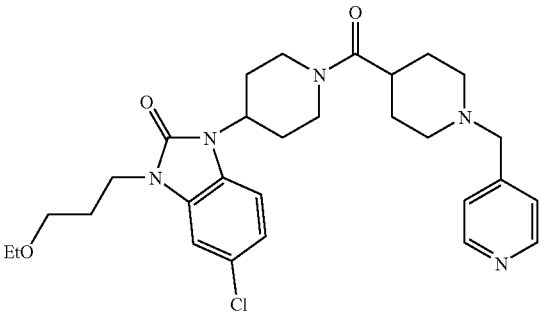 | 540 (MH+) |
| 1AS | 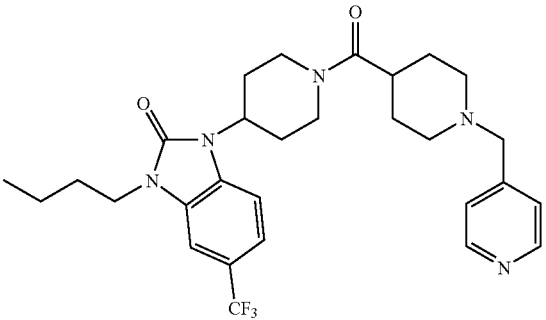 | 544 (MH+) |
| 1AT | 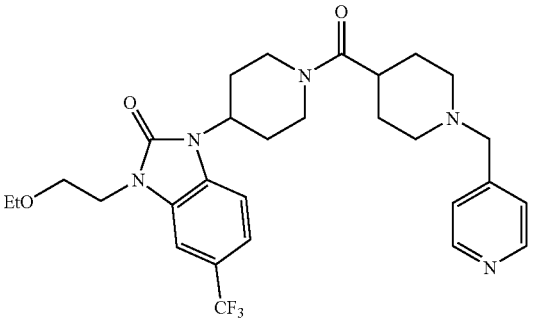 | 560 (MH+) |
| 1AU | 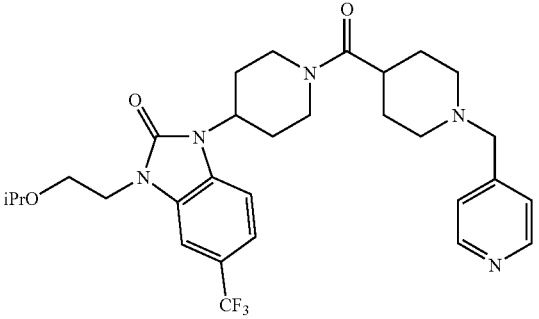 | 574 (MH+) |

-continued

| Compound | MS(Cl, FAB, ES) |
| --- | --- |
| 1AV | 574 (MH+) |
| 1AW | 559 (MH+) |
| 1AX | 599 (MH+) |
| 1AY | 601 (MH+) |

-continued

| Compound | MS(Cl, FAB, ES) |
| --- | --- |
| 1AZ | 532 (MH+) |
| 1AAA | 560 (MH+) |

The following compounds were prepared using a procedure similar to the above, but using Preparation 2 as starting material. The enantiomers were separated on a Chiralcel OD column (eluant: isopropanol—hexane with diethylamine).

| Compound | MS (Cl, FAB, ES) |
| --- | --- |
| 1BA | 434 (MH+) |
| 1BB | 502 (MH+) |

| Compound | MS (CI, FAB, ES) |
|---|---|
| 1BC [structure] | 492 (MH⁺) |
| 1BD [structure] | 526 (MH⁺) |
| 1BE [structure] | 581 (MH⁺) |
| 1BF [structure] | 540 (MH⁺) |

The following compounds were prepared using a procedure similar to the above but using Preparation 3 as starting material.

| Compound | | MS (Cl, FAB, ES) |
|---|---|---|
| 1CA | | 438 (MH+) |
| 1CB | | 506 (MH+) |

EXAMPLE 2

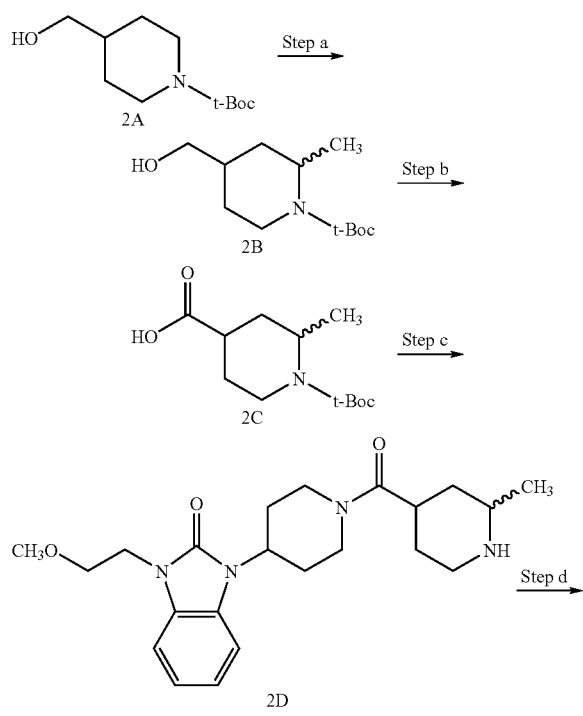

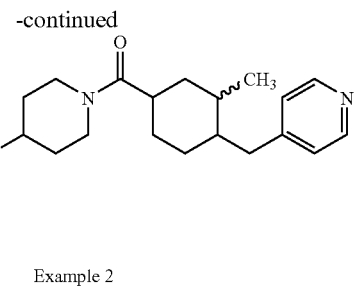

Example 2

Step a: A flask was charged with alcohol 2A (5.40 g, 25.08 mmol) and DMF (50 ml). Imidazole (1.88 g, 27.59 mmol) and TBDMS chloride (3.40 g, 22.57 mmol) were added at 23° C. After 16 h, saturated NH$_4$Cl (500 ml) was added and the product extracted with EtOAc. The combined organic extracts were washed with brine, dried (Na$_2$SO$_4$), filtered, and concentrated. Purification by silica gel chromatography (eluant: hexane, then 8:1 hexane:EtOAc) afforded 6.54 g (19.85 mmol, 79%) of the TBMDS protected alcohol. MS (FAB for M+1): m/e 230.

The TBDMS protected alcohol (5.54 g, 16.8 mmol) was dissolved in Et$_2$O (50 ml) and cooled to −78° C. under N$_2$. TMEDA (2.44 g, 3.2 ml, 21.0 mmol) and sec-BuLi (1.3 M, 16.2 ml, 21.0 mmol) were added via syringe and the reaction stirred at −78° C. After 3 h, dimethylsulfate (3.18 g, 2.4 ml, 25.2 mmol) was added via syringe, and the reaction was allowed to warm slowly over 2 h to 23° C. and stirred for an additional 2 h. The reaction was quenched by addition of water (100 ml) and the product extracted with EtOAc. The combined organic extracts were dried (MgSO$_4$), filtered, and concentrated. Purification by silica gel chromatography (eluant: 5% EtOAc-hexane then 10% EtOAc-hexane) gave 4.59 g (13.36 mmol, 79%) of the 2-methylated product as a colorless oil. MS (FAB for M+1): m/e 344.

The 2-methylated product (4.58 g, 13.3 mmol) was dissolved in THF (30 ml) and n-Bu$_4$NF (1.0 M in THF, 20.0 ml, 20.0 mmol) was added. After 16 h at 23° C., water (100 ml) was added and the product extracted with EtOAc. The combined organic extracts were dried (MgSO$_4$), filtered, and concentrated. Purification by silica gel chromatography (eluant: 5% CH$_3$OH—CH$_2$Cl$_2$ then 10% CH$_3$OH—CH$_2$Cl$_2$) gave 3.06 g (13.3 mmol, 100%) of 2B as a colorless oil. MS (FAB for M+1): m/e 230.

Step b: Oxalyl chloride (2.57 g, 1.8 ml, 20.3 mmol) and dry CH$_2$Cl$_2$ (60 ml) were cooled to −78° C. under N$_2$. DMSO (3.16 g, 2.9 ml, 40.5 mmol) in CH$_2$Cl$_2$ (5 ml) was added dropwise via an addition funnel. After 15 min at −78° C., compound 2B as a solution in CH$_2$Cl$_2$ (20 ml) was added dropwise. After 1 h at −78° C., Et$_3$N (5.46 g, 7.5 ml, 54.0 mmol) was added and the reaction allowed to warm up to 23° C. After 2 h, water (100 ml) was added and the product extracted with CH$_2$Cl$_2$. The combined organic extracts were dried (MgSO$_4$), filtered, and concentrated to give 3.07 g (13.5 mmol, 100%) of the corresponding aldehyde as a yellow oil. MS (ES for M+1): m/e 228.

To the aldehyde (3.07 g, 13.5 mmol) dissolved in t-BuOH (60 ml) was added 2-methyl-2-butene (6 ml), sodium chlorite (7.33 g, 81.0 mmol), and potassium phosphate (9.19 g, 67.5 mmol) in H$_2$O (60 ml). The reaction was stirred at 23° C. After 2 h, the solvent was removed, 0.5 N HCl added and the product extracted with CH$_2$Cl$_2$. The combined organic extracts were dried (MgSO$_4$), filtered, and concentrated to give 3.29 g (13.5 mmol, 100%) of the acid 2C as a yellow oil. MS (FAB for M+1): m/e 244.

Step c: 2C was coupled with the appropriate piperidine to afford intermediate 2D, which was transformed into the title compound using the procedure of Example 1, Step G. (ES for M+1): m/e 492.

EXAMPLE 3

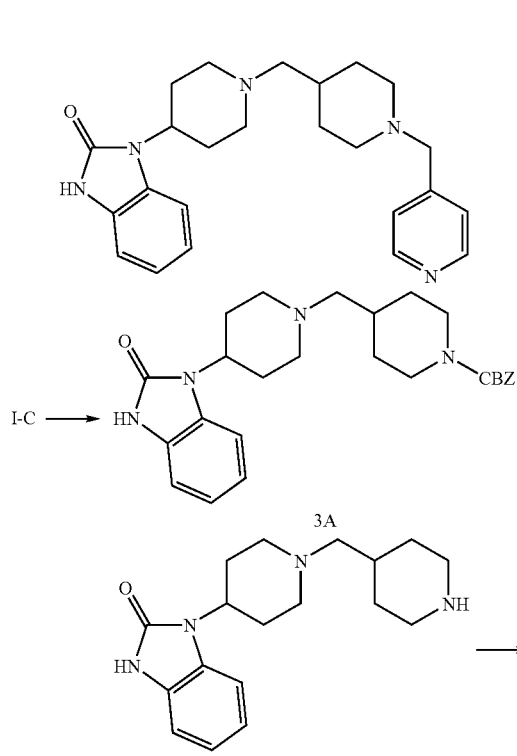

Compound I-C (2.64 g, 12.13 mmol), N—CBZ-4-piperidinecarboxaldehyde (2.00 g, 8.09 mmol), crushed 3 Å molecular sieves (2.5 g), and NaBH(OAc)$_3$ (2.57 g, 12.13 mmol) were combined in CH$_2$Cl$_2$:CF$_3$CH$_2$OH (1:1, 50 ml) at 23° C. The reaction was stirred for 16 h and then quenched with 1 N NaOH (50 ml). The reaction mixture was then filtered, the solid washed with CH$_2$Cl$_2$ and the filtrate transferred to a separatory funnel. The combined organic extracts were dried (MgSO$_4$), filtered, and concentrated. Further purification by silica gel chromatography (eluant: 5% CH$_3$OH—CH$_2$Cl$_2$ then 10% CH$_3$OH—CH$_2$Cl$_2$) gave 3.34 g (7.45 mmol, 92% yield) of the product 3A as a white foam. MS (FAB for M+1): m/e 449.

Compound 3A (3.33 g, 7.42 mmol) was dissolved in DMF (50 ml) and shaken on Parr hydrogenation apparatus under 50 psi hydrogen pressure with 10% Pd/C catalyst (0.75 g). After 20 h, the reaction was filtered through celite and washed with CH$_3$OH. The filtrate was concentrated to give 2.16 g (6.87 mmol, 93% yield) of 3B as a white solid. MS (Cl for M+1): m/e 315.

3B (1.00 g, 3.18 mmol) was added to trifluoroethanol (25 ml), 4-pyridine-carboxaldehyde (0.31 g, 2.89 mmol), crushed 3 Å molecular sieves (1.0 g) and NaBH(OAc)$_3$ (0.92 g, 4.34 mmol) at 23° C. After 16 h, 1 N NaOH (50 ml) was added, the reaction mixture filtered and the filtrate transferred to a separatory funnel. The combined organic extracts were dried (MgSO$_4$), filtered, and concentrated. Purification by silica gel chromatography (eluant: 5% CH$_3$OH with NH$_3$—CH$_2$Cl$_2$ then 7% CH$_3$OH with NH$_3$—CH$_2$Cl$_2$) gave 0.54 g (1.33 mmol, 46%) of the title compound as a white foam. MS (ES for M+1): m/e 406.

EXAMPLE 4

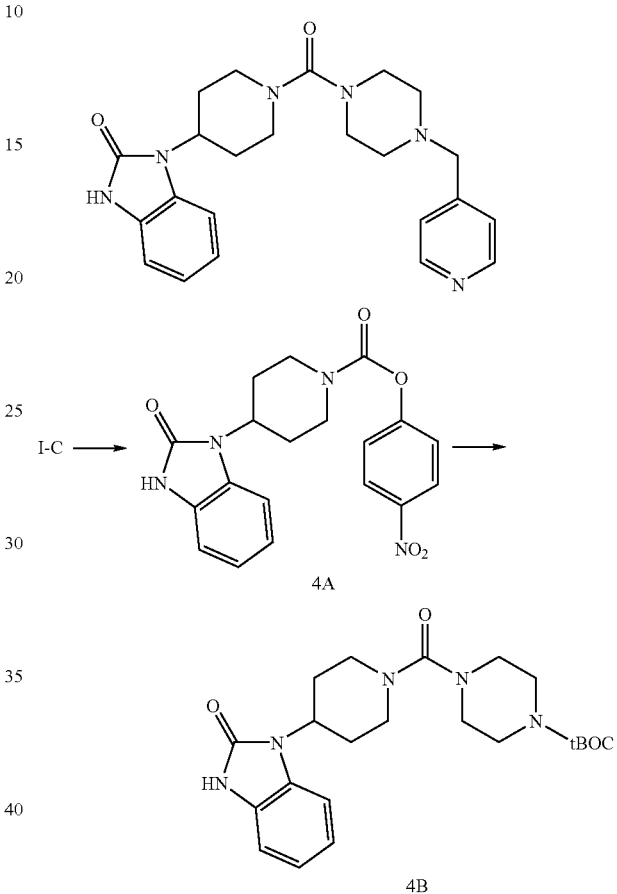

Compound I-C (4.00 g, 18.4 mol) was dissolved in dichloroethane (100 ml) and Et$_3$N (2.79 g, 3.8 ml, 27.6 mmol) and 4-nitrophenyl chloroformate (3.71 g, 18.4 mmol) were added. The reaction was heated at reflux for 1 h, cooled, and 0.5 N NaOH (100 ml) was added. The product was extracted with CH$_2$Cl$_2$, the combined organic extracts were dried (MgSO$_4$), filtered, and concentrated to give 7.04 g (18.4 mmol, 100%) of 4A as a yellow foam.

Compound 4A (3.5 g, 9.2 mmol) was dissolved in DMF (50 ml) and mono-N-tBOC-piperazine (1.7 g, 9.2 mmol) was added. The reaction was heated at 120° C. for 16 h, concentrated, and the residue dissolved in water. The product was extracted with CH$_2$Cl$_2$ and the combined extracts were dried (MgSO$_4$), filtered, and concentrated. Purification by silica gel chromatography (eluant: 5% CH$_3$OH—CH$_2$Cl$_2$) gave 1.6 g (3.73 mmol, 41% yield) of 4B as a yellow foam. MS (FAB for M+1): m/e 430.

Compound 4B was deprotected as in Intermediate 3, Step D and reacted with the pyridinecarboxaldehyde as in Example 3 to obtain the title compound.

EXAMPLE 5

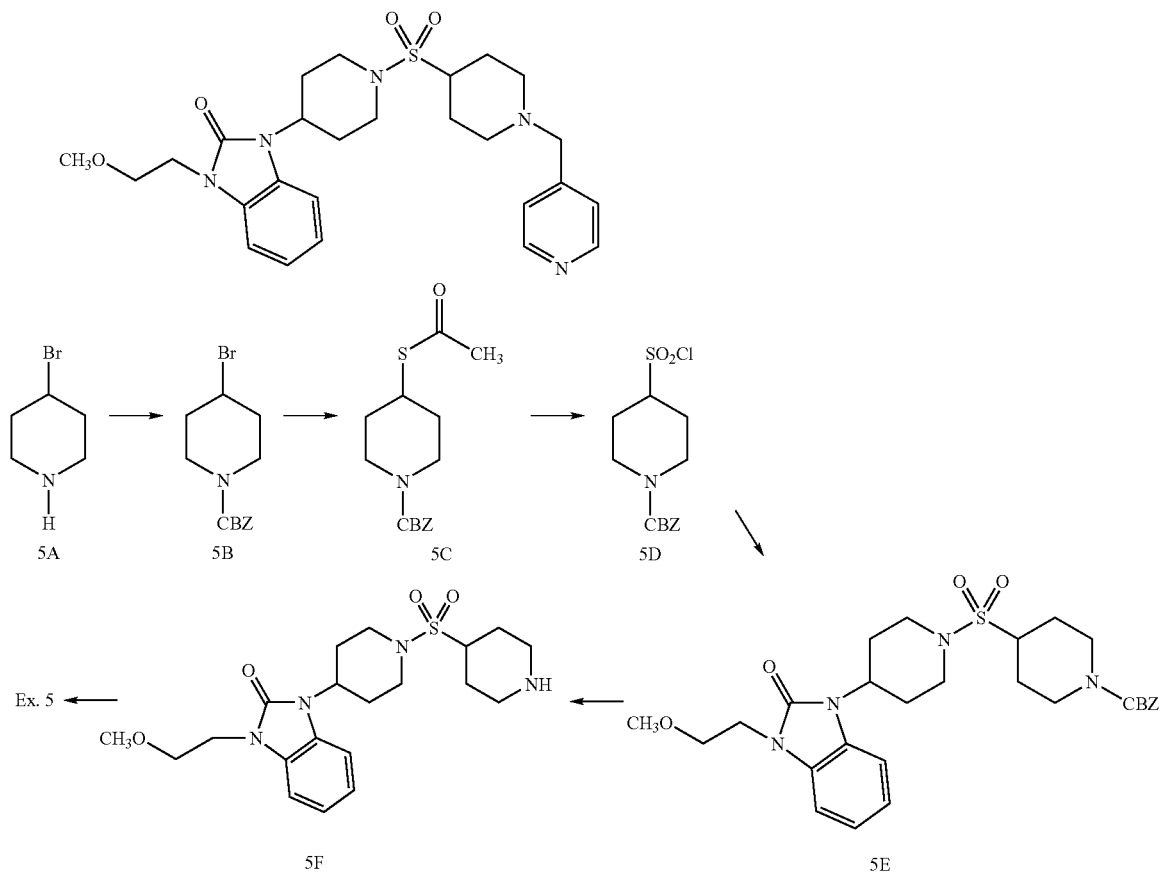

A flask was charged with compound 5A (HBr salt) (5.0 g, 20.4 mmol), CH$_2$Cl$_2$ (80 ml), saturated NaHCO$_3$ (160 ml) and benzyl chloroformate (3.7 ml, 24.5 mmol) at 23° C. After 22 h, the biphasic reaction mixture was transferred to a separatory funnel, and the product extracted with CH$_2$Cl$_2$. The combined organic extracts were washed with brine, dried (Na$_2$SO$_4$), filtered, and concentrated. Purification by silica gel chromatography (eluant: 8:1 hexane:EtOAc) gave 3.02 g (10.1 mmol, 50% yield) of 5B as a colorless oil. MS: m/e 298.

To a solution of 5B (2.13 g, 7.14 mmol) in dry DMSO (12 ml) was added potassium thioacetate (1.23 g, 10.7 mmol). After 21.5 h, water was added and the product extracted into EtOAc. The combined organic extracts were washed with brine, dried (Na$_2$SO$_4$), filtered, and concentrated. Purification by silica gel chromatography (eluant: 5:1 hexane:EtOAc) gave 1.36 g (4.7 mmol, 66% yield) of 5C as a yellow oil. MS: m/e 294.

Cl$_2$ (gas) was bubbled into a suspension of 5C (1.05 g, 3.58 mmol) in water (30 ml) at 0° C. After 35 min, additional water was added, and the product extracted with Et$_2$O. The combined organic extracts were washed sequentially with 5% Na$_2$S$_2$O$_5$ (100 ml), saturated NaHCO$_3$ (50 ml), and brine. The organic layer was dried (Na$_2$SO$_4$), filtered, and concentrated. Purification by silica gel chromatography (eluant: 5:1 hexane:EtOAc, followed by hexane:EtOAc 3.5:1) gave 0.909 g (2.86 mmol, 80% yield) of 5D as a yellow solid. MS: m/e 318.

To a solution of 5D (227 mg, 0.714 mmol) in CH$_2$Cl$_2$ (8 ml) at 0° C. was added Et$_3$N (0.30 ml, 2.14 mmol) and 4-(2-keto-3-methoxyethyl-1-benzimidazolinyl)-piperidine (289 mg, 0.93 mmol). After 1 h at 0° C., water was added and the product extracted with CH$_2$Cl$_2$. The combined organic extracts were washed with 1 N HCl, brine and then dried (Na$_2$SO$_4$), filtered, and concentrated. The crude product 5E (0.54 mmol, 76% yield) was used without further purification. MS: mle 557.

To a solution of 5E (300 mg, 53.9 mmol) in CH$_3$OH (10 ml) was added palladium on charcoal (50 mg) in a pressure vessel. The reaction mixture was shaken under hydrogen (50 psi) for 14 h. The catalyst was removed by filtration, the filtrate concentrated and purified by silica gel chromatography (eluant: 18:1 CH$_2$Cl$_2$:4% NH$_3$ in CH$_3$OH) to give 0.198 g (0.47 mmol, 87% yield) of 5F as a white solid. MS: m/e 423 (M+1).

To a solution of 5F (180 mg, 0.426 mmol) in CH$_2$Cl$_2$ (4 ml) was added 3 Å molecular sieves (400 mg), 4-pyridinecarboxyaldehyde (137 mg, 1.28 mmol) and NaB(OAc)$_3$H (271 mg, 1.28 mmol). After 24 h at 23° C. the reaction was filtered, additional CH$_2$Cl$_2$ added, and the organic phase washed with 1 N NaOH, and brine. The organic layer was separated, dried (Na$_2$SO$_4$), filtered, and concentrated. Purification by silica gel chromatography (eluant: 18:1 CH$_2$Cl$_2$: 4% NH$_3$ in CH$_3$OH) afforded 0.064 g (0.124 mmol, 30% yield) of the title compound as a white solid. MS: m/e 514 (M+1).

EXAMPLE 6

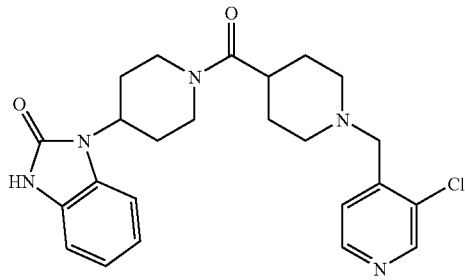

Intermediate 6 (I-L) was deprotected using the procedure of Intermediate 3, Step D. To a solution of the hydrochloride salt of the resulting compound (1.50 g, 4.11 mmol) in trifluoroethanol (20 ml) was added potassium t-butoxide (0.37 g, 3.29 mmol), crushed 3 Å molecular sieves (1.5 g), 3-chloro-4-pyridinecarboxaldehyde (0.39 g, 2.74 mmol), and NaBH(OAc)$_3$ (0.87 g, 4.11 mmol). After 16 h, the reaction was filtered, the solvent evaporated, and the residue redissolved in CH$_2$Cl$_2$. 0.5 N NaOH (30 ml) was added and the product extracted with CH$_2$Cl$_2$. The combined organic extracts were dried (MgSO$_4$), filtered, and concentrated. Purification by silica gel chromatography (eluant: 5% MeOH—CH$_2$Cl$_2$) gave 0.85 g (1.87 mmol, 65% yield) of the title compound as a light yellow foam. MS (FAB for M+1): m/e 454.

The following compounds were prepared using a similar above procedure with the appropriate pyridinecarboxaldehyde analog:

| Compound | MS (Cl, FAB, or ES) |
|---|---|
| 6A | 434 (MH$^+$) |
| 6B | 476 (MH$^+$) |
| 6C | 510 (MH$^+$) |

-continued

| Compound | MS (Cl, FAB, or ES) |
|---|---|
| 6D | 436 (MH+) |
| 6E | 420 (MH+) |
| 6F | 420 (MH+) |
| 6G | 488 (MH+) |
| 6H | 498 (MH+) |

-continued

| Compound | MS (Cl, FAB, or ES) |
| --- | --- |
| 6I | 505 (MH⁺) |
| 6J | 574 (MH⁺) |
| 6K | 636 (MH⁺) |
| 6L | 622 (MH⁺) |

| -continued | |
|---|---|
| Compound | MS (Cl, FAB, or ES) |
| 6M 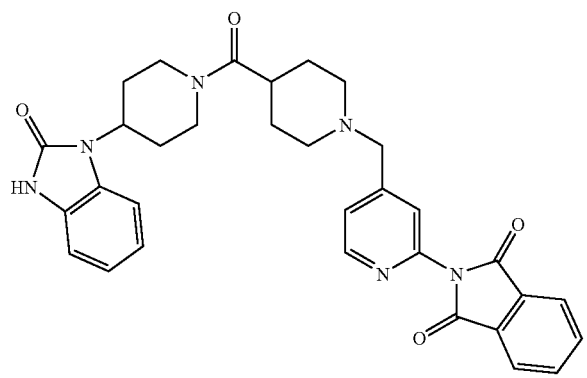 | 434 (MH+) |

EXAMPLE 7

To a solution of deprotected I-L (100 mg, 0.271 mmol) and Preparation 5-2B (250 mg of mixture, ~0.33 mmol) in DMF was added Et$_3$N (0.5 ml, ~3.6 mmol). The reaction mixture was stirred at 23° C. for 15 h, water was added, and the mixture extracted with CH$_2$Cl$_2$. The combined organic extracts were washed with water, dried, and concentrated. Purification by silica gel chromatography (eluant: 10% CH$_3$OH—CH$_2$Cl$_2$) provided the title compound as a slightly yellow solid. (62 mg, 41% yield). MS (Cl): 597 (MH+ +CH$_3$OH).

The following compounds were prepared in a similar manner:

| Compounds | MS (Cl) |
|---|---|
| 7A | 579 (MH+) |
| 7B | 655 (MH+ +CH$_3$OH) |

-continued

| Compounds | MS (Cl) |
|---|---|
| 7C | 710 (MH$^+$+CH$_3$OH) |
| 7D | 735 (MH$^+$+CH$_3$OH) |
| 7E | 641 (MH$^+$) |
| 7F | 696 (MH$^+$) |

|Compounds| |MS (Cl)|
|---|---|---|
|7G| |673 (MH+)|
|7H| |719 (MH+)|
|7I| |—|
|7J| |—|

| Compounds | MS (Cl) |
|---|---|
| 7K | — |
| 7L | 500 (MH+) |
| 7M | 512 (MH+) |
| 7N | 556 (MH+) |

| Compounds | MS (Cl) |
|---|---|
| 7O | — |
| 7P | — |
| 7Q | — |
| 7R | — |

-continued

| Compounds | MS (Cl) |
|---|---|
| 7S | — |
| 7T | — |
| 7U | — |
| 7V | 564 (MH⁺) |

EXAMPLE 8

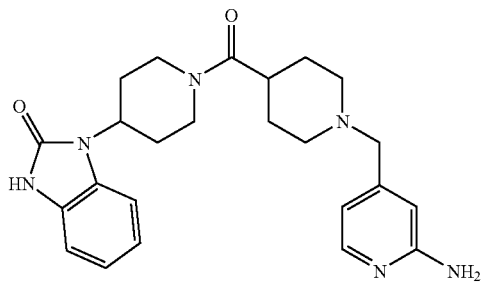

To a solution of hydrazine (1 ml of 0.5 M, 0.50 mmol) in ethanol was added the compound of Example 7 (51 mg, 0.090 mmol). The reaction mixture was stirred at 23° C. for 1.5 h, diluted with aqueous $NaHCO_3$, and extracted with $CH_2Cl_2$. The combined organic extracts were washed with water, dried, and concentrated. Purification by silica gel chromatography (eluant: 10:90:1 $CH_3OH:CH_2Cl_2:NH_4OH$) gave the title compound as a white solid (20.4 mg, 52% yield). MS (Cl) 435 ($MH^+$).

Using the compounds of Example 7, the following compounds were prepared according to a similar procedure.

| Compounds | MS (Cl) |
|---|---|
| 8A | 449 ($MH^+$) |
| 8B | 493 ($MH^+$) |
| 8C | 548 ($MH^+$) |
| 8D | 573 ($MH^+$) |

| Compounds | MS (CI) |
|---|---|
| 8E 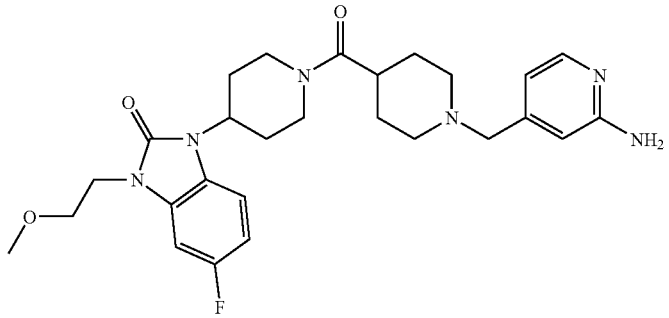 | 511 (MH+) |
| 8F 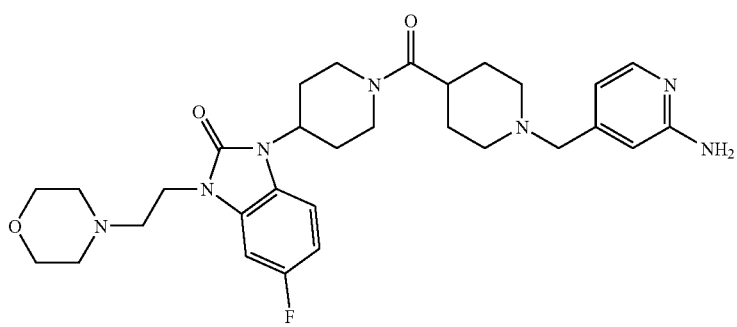 | 566 (MH+) |
| 8G 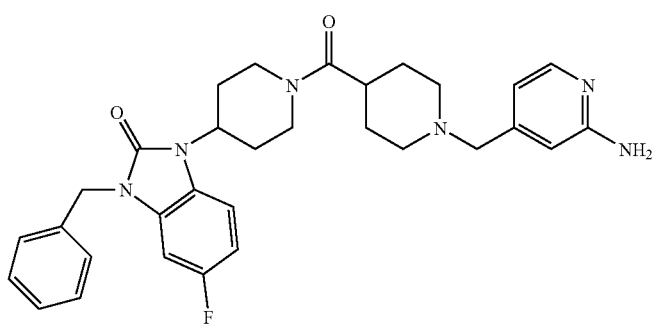 | 543 (MH+) |
| 8H 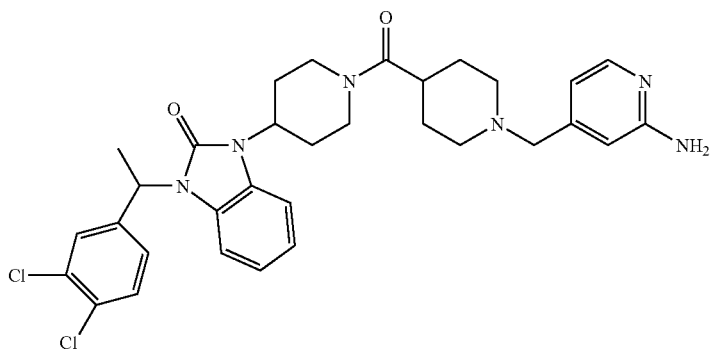 | 607 (MH+) |

-continued

| Compounds | MS (Cl) |
|---|---|
| 8I | 633 (MH+) |
| 8J | 625 (MH+) |
| 8K | 651 (MH+) |
| 8L | 449 (MH+) |

| Compounds | MS (CI) |
|---|---|
| 8M | 493 (MH⁺) |
| 8N | 548 (MH⁺) |
| 8O | 607 (M-NH₃) |
| 8P | 573 (MH⁺) |

-continued
| Compounds | MS (Cl) |
|---|---|
| 8Q | 511 (MH+) |
| 8R | 633 (MH+) |
| 8S | 435 (MH+) |
EXAMPLE 9
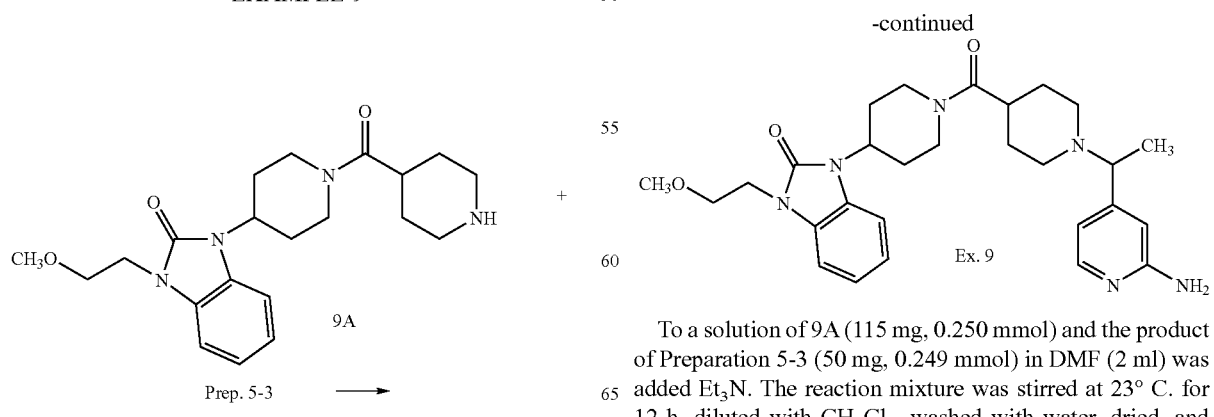
To a solution of 9A (115 mg, 0.250 mmol) and the product of Preparation 5-3 (50 mg, 0.249 mmol) in DMF (2 ml) was added Et$_3$N. The reaction mixture was stirred at 23° C. for 12 h, diluted with CH$_2$Cl$_2$, washed with water, dried, and concentrated. Purification of the residue by preparative TLC (10% CH₃OH—CH₂Cl₂) afforded a white solid. (34 mg, 27% yield). MS (Cl) 507 (MH⁺).

The following compounds were synthesized using a similar procedure.

| | Compound | MS (Cl) |
|---|---|---|
| 9B | | 525 (MH⁺) |
| 9C | | 580 (MH⁺) |
| 9D | | 639 (MH⁺) |
| 9E | | 557 (MH⁺) |

-continued

| Compound | MS (Cl) |
|---|---|
| 9F 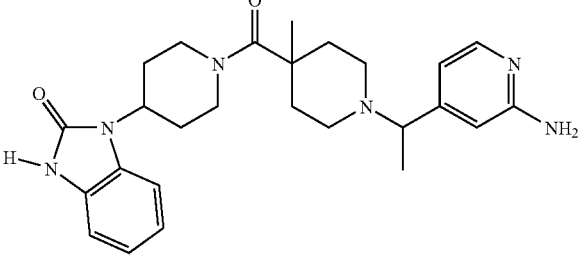 | 463 (MH+) |
| 9G 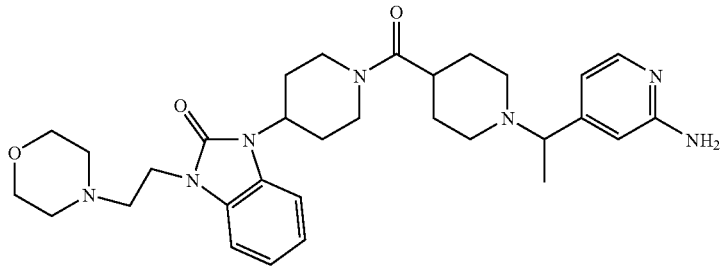 | 561 (M) |
| 9H 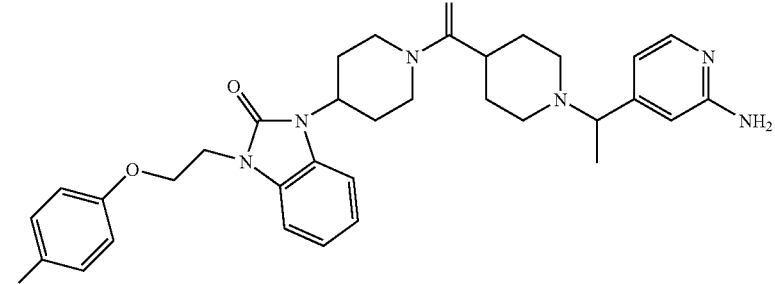 | 587 (MH+) |

EXAMPLE 10

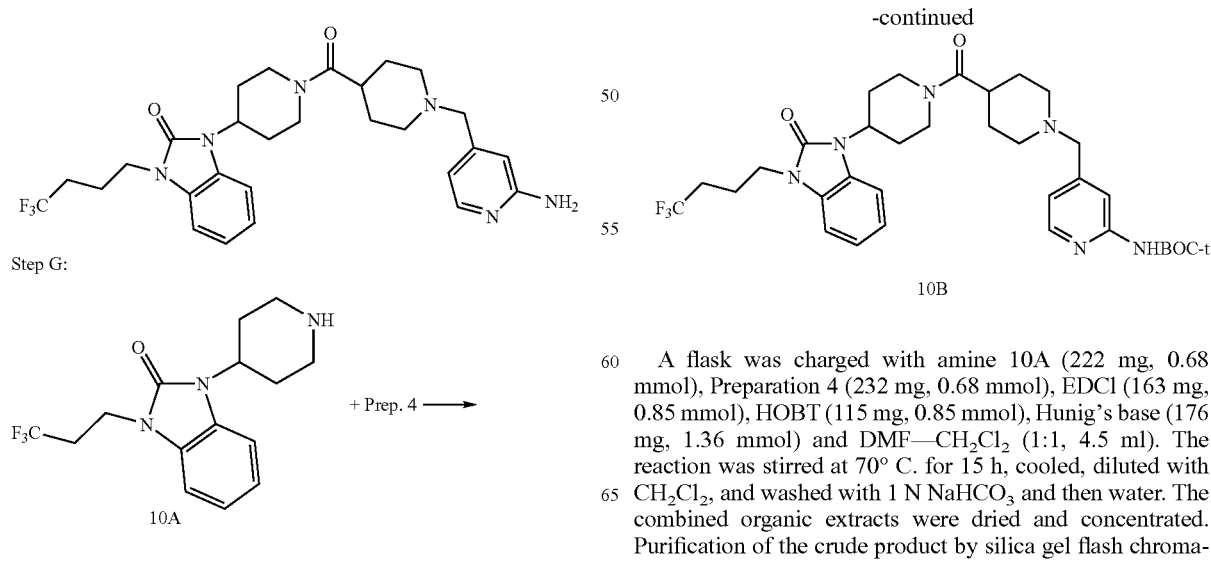

Step G:

10A + Prep. 4 ⟶

10B

A flask was charged with amine 10A (222 mg, 0.68 mmol), Preparation 4 (232 mg, 0.68 mmol), EDCl (163 mg, 0.85 mmol), HOBT (115 mg, 0.85 mmol), Hunig's base (176 mg, 1.36 mmol) and DMF—$CH_2Cl_2$ (1:1, 4.5 ml). The reaction was stirred at 70° C. for 15 h, cooled, diluted with $CH_2Cl_2$, and washed with 1 N $NaHCO_3$ and then water. The combined organic extracts were dried and concentrated. Purification of the crude product by silica gel flash chromatography (eluant: 5% CH$_3$OH—CH$_2$Cl$_2$) gave 10B as a white solid (243 mg, 55% yield).

Compounds with different substituents on the benzimidazolone portion were similarly prepared.

Step G':

TFA (2 ml) was added to a solution of 10B (230 mg, 0.36 mmol) in CH$_2$Cl$_2$ (4 ml). The resulting mixture was stirred at 23° C. for two days, diluted with CH$_2$Cl$_2$, and washed with 1 N NaOH. The organic layer was dried and concentrated to afford the crude product. Purification of the residue via preparative TLC plate (10% CH$_3$OH—CH$_2$Cl$_2$) afforded the title compound as a white solid (177 mg, 90% yield).

The following compounds were synthesized by the same reaction:

| | Compound | MS (CI) |
|---|---|---|
| 10C | | 560 (MH$^+$) |
| 10D | | 541 (MH$^+$) |
| 10E | | 564 (MH$^+$) |
| 10F | | 549 (MH$^+$) |

-continued

| | Compound | MS (Cl) |
|---|---|---|
| 10G | | 563 (MH+) |
| 10H | | 549 (MH+) |
| 10I | | 521 (MH+) |
| 10J | | 509 (MH+) |

Using the procedures similar to those above, with the appropriate starting materials, the following compounds were prepared:

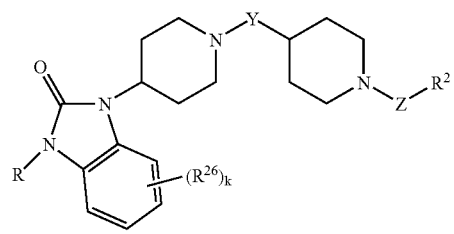

| Ex. | R | $(R^{26})_k$ | Y | Z | $R^2$ | Physical Data |
|---|---|---|---|---|---|---|
| 11 | H | H | —C(O)— | —CH$_2$— | 4-isoquinolinyl | 470 (MH$^+$) |
| 12 | HOOC-CH$_2$- | H | —C(O)— | —CH$_2$— | 4-pyridyl | 478 (MH$^+$) |
| 13 | CH$_3$(CH$_2$)$_3$— | H | —C(O)— | —CH(CH$_3$)— | 4-pyridyl | 490 (MH$^+$) isomer 1 |
| 14 | CH$_3$(CH$_2$)$_3$— | H | —C(O)— | —CH(CH$_3$)— | 4-pyridyl | 490 (MH$^+$) isomer 2 |
| 15 | CH$_3$O(CH$_2$)$_2$— | H | —C(O)— | —CH(CN)— | 4-pyridyl | 503 (MH$^+$) |
| 16 | CH$_3$O(CH$_2$)$_2$— | H | —C(O)— | —C(CH$_3$)$_2$— | 4-pyridyl | 506 (MH$^+$) |
| 17 | H | H | —C(O)— | bond | 4-methyl-2-pyridyl | 420 (MH$^+$) |
| 18 | CH$_3$O(CH$_2$)$_2$— | 5-F | —C(O)— | —CH$_2$— | 4-pyridyl | 496 (MH$^+$) |
| 19 | CH$_3$O(CH$_2$)$_2$— | 5-F | —C(O)— | —CH(CH$_3$)— | 4-pyridyl | 510 (MH$^+$) |

-continued

| # | R1 | R2 | X | Y | Ar | MS |
|---|---|---|---|---|---|---|
| 20 | morpholinopropyl | 5-F | —C(O)— | —CH₂— | 4-pyridyl | 551 (MH⁺) |
| 21 | morpholinopropyl | 5-F | —C(O)— | —CH(CH₃)— | 4-pyridyl | 565 (MH⁺) |
| 22 | H | 5-F | —C(O)— | —CH₂— | 4-pyridyl | 438 (MH⁺) |
| 23 | H | 5-F | —C(O)— | —CH(CH₃)— | 4-pyridyl | 452 (MH⁺) |
| 24 | H | 5-Cl | —C(O)— | —CH₂— | 4-pyridyl | 454 (MH⁺) |
| 25 | CH₃— | 5-F | —C(O)— | —CH₂— | 4-pyridyl | 469 (MH⁺) |
| 26 | C₆H₅—CH₂— | 5-Cl | —C(O)— | —CH₂— | 4-pyridyl | 545 (MH⁺) |
| 27 | morpholinopropyl | 5-Cl | —C(O)— | —CH₂— | 4-pyridyl | 568 (MH⁺) |
| 28 | morpholinopropyl | 5-Cl | —C(O)— | —CH(CH₃)— | 4-pyridyl | 582 (MH⁺) isomer 1 |
| 29 | morpholinopropyl | 5-Cl | —C(O)— | —CH(CH₃)— | 4-pyridyl | 582 (MH⁺) isomer 2 |
| 30 | H | 5-CF₃— | —C(O)— | —CH₂— | 4-pyridyl | 488 (MH⁺) |
| 31 | H | H | —C(O)CH₂— | —CH₂— | 4-pyridyl | 434 (MH⁺) |

-continued
| | | | | | | |
|---|---|---|---|---|---|---|
| 32 | CH₃O(CH₂)₂— | H | —C(O)CH₂— | bond | 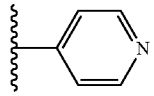 | 478 (MH⁺) |
| 33 | CH₃O(CH₂)₂— | H | —C(O)CH₂— | bond | 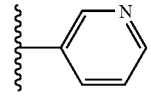 | 478 (MH⁺) |
| 34 | H | 5-CF₃ | —C(O)NH— | —CH₂— | 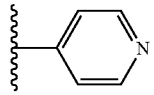 | 503 (MH⁺) |
| 35 | H | 5-CF₃ | —SO₂— | —CH₂— | 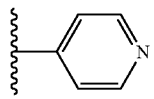 | 523 (MH⁺) |
| 36 | H | 5-CF₃ | (=N—CN)—NH— | —CH₂— | 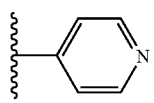 | 527 (MH⁺) |
| 37 | H | H | —C(O)— | bond | 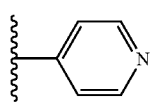 | 406 (MH⁺) |
| 38 | H | H | —C(O)— | —C(O)— | 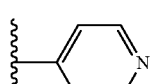 | 434 (MH⁺) |
| 39 | H | H | —C(O)— | —(CH₂)₂— | 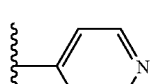 | 434 (MH⁺) |
| 40 | H | H | —C(O)— | —C(O)CH₂— | 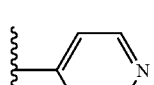 | 448 (MH⁺) |
| 41 | H | 5-CF₃ | —C(O)— | bond | 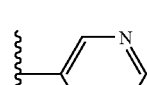 | 474 (MH⁺) |
| 42 | CH₃O(CH₂)₂— | H | —C(O)— | —C(=NH)— | 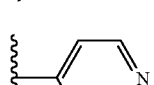 | 491 (MH⁺) |
| 43 | CH₃O(CH₂)₂— | H | —C(O)— | —C(O)— | 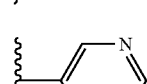 | 492 (MH⁺) |
| 44 | H | 5-CF₃ | —C(O)— | —C(O)— | 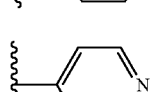 | 502 (MH⁺) |
| 45 | CH₃O(CH₂)₂— | H | —C(O)— | —C(O)NH— | 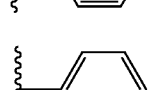 | 507 (MH⁺) |

-continued

| | | | | | | |
|---|---|---|---|---|---|---|
| 46 | CH₃O(CH₂)₂— | H | —C(O)— | —C(O)— | 3-pyridyl N-oxide | 508 (MH⁺) |
| 47 | H | 5-CF₃ | —C(O)— | —NH—C(O)— | 2-pyridyl | 517 (MH⁺) |
| 48 | H | 5-CF₃ | —C(O)— | —NH—C(O)— | 4-pyridyl | 517 (MH⁺) |
| 49 | CH₃O(CH₂)₂— | H | —C(O)— | bond | 5,6,7,8-tetrahydroisoquinolin-5-yl | 518 (MH⁺) |
| 50 | CH₃O(CH₂)₂— | H | —C(O)— | —CH₂—C(O)—NH— | 4-pyridyl | 521 (MH⁺) |
| 51 | CH₃O(CH₂)₂— | H | —C(O)— | —C(O)—NH—CH₂— | 4-pyridyl | 521 (MH⁺) |
| 52 | CH₃O(CH₂)₂— | H | —C(O)— | bond | 3-(4-pyridyl)phenyl | 540 (MH⁺) |
| 53 | CH₃O(CH₂)₂— | H | —C(O)— | =N—N=N—NH—CH₂— (with CN) | 3-pyridyl | 507 (MH⁺) |
| 54 | CH₃O(CH₂)₂— | 5-CF₃ | —C(O)— | —(CH₂)₃— | 4-pyridyl | 574 (MH⁺) |
| 55 | CH₃O(CH₂)₂— | 5-CF₃ | —C(O)— | —(CH₂)₃— | 3-pyridyl | 574 (MH⁺) |
| 56 | CH₃O(CH₂)₂— | 5-CF₃ | —C(O)— | —C(O)—(CH₂)₂— | 4-pyridyl | 588 (MH⁺) |
| 57 | CH₃O(CH₂)₂— | 5-CF₃ | —C(O)— | —(CH₂)₄— | 4-pyridyl | 588 (MH⁺) |

US 7,220,735 B2
| | 111 | | | | 112 | |
|---|---|---|---|---|---|---|
| 58 | CH₃O(CH₂)₂— | H | —C(O)— | —CH₂— | 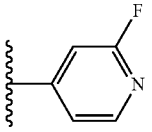 | 496 (MH⁺) |
| 59 | H | 5-CF₃ | —C(O)— | —(CH₂)₄— | 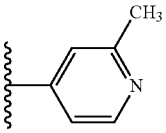 | 502 (MH⁺) |
| 60 | 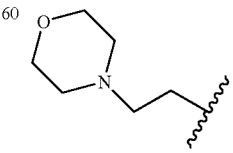 | H | —C(O)— | —CH₂— | 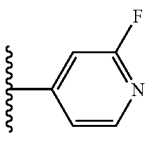 | 551 (MH⁺) |
| 61 | H | H | —C(O)— | —CH(CH₃)— | 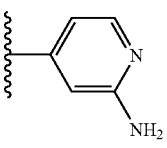 | 449 (MH⁺) |
| 62 | 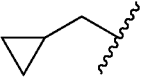 | 5-F | —C(O)— | —CH₂— | 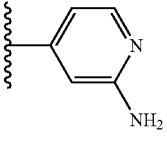 | 507 (MH⁺) |
| 63 | 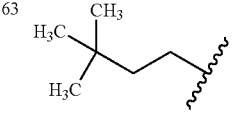 | 5-F | —C(O)— | —CH₂— | 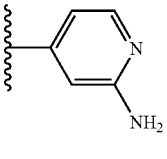 | 537 (MH⁺) |
| 64 | 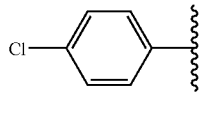 | H | —C(O)— | —CH₂— | 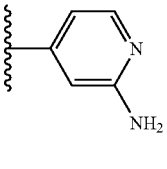 | 546 (MH⁺) |
| 65 | 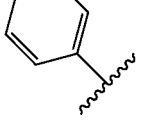 | 5-Cl | —C(O)— | —CH₂— | 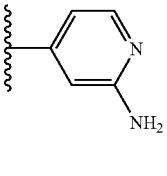 | 547 (MH⁺) |
| 66 | 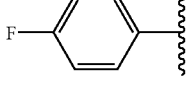 | 5-Cl | —C(O)— | —CH₂— | 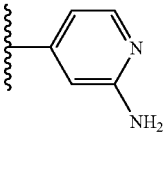 | 564 (MH⁺) |
| 67 | H | 5-CF₃— | —C(O)— | —NH—C(O)— | 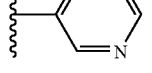 | 517 (MH⁺) |

-continued
| | | | | | | |
|---|---|---|---|---|---|---|
| 68 | CH₃O(CH₂)₂— | 5-CF₃— | —C(O)— | bond | 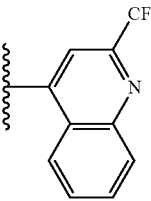 | 650 (MH⁺) |
| 69 | CH₃O(CH₂)₂— | H | —C(O)— | —CH₂— | 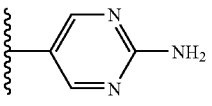 | 494 (MH⁺) |
| 70 | CH₃O(CH₂)₂— | H | —C(O)— | —CH₂— | 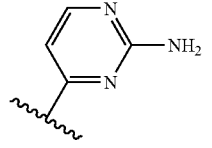 | 494 (MH⁺) |
| 71 | CH₃O(CH₂)₂— | H | —C(O)— | —CH₂— | 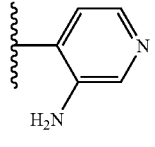 | 493 (MH⁺) |
| 72 | 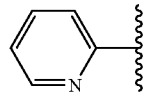 | 5-F | —C(O)— | —CH₂— | 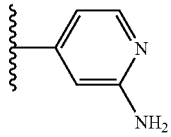 | 530 (MH⁺) |
| 73 | 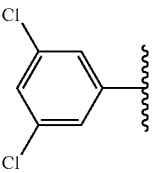 | 5-F | —C(O)— | —CH₂— | 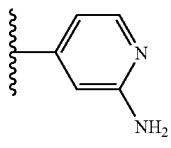 | 598 (MH⁺) |
| 74 | 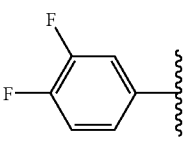 | 5-F | —C(O)— | —CH₂— | 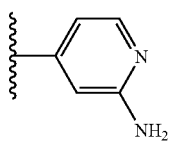 | 565 (MH⁺) |
| 75 | 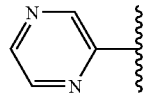 | 5-F | —C(O)— | —CH₂— | 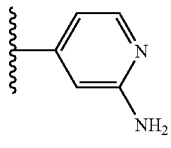 | 531 (MH⁺) |
| 76 | 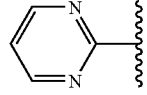 | 5-F | —C(O)— | —CH₂— | 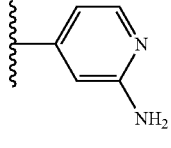 | 531 (MH⁺) |
| 77 | 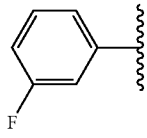 | 5-F | —C(O)— | —CH₂— | 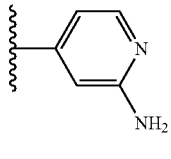 | 547 (MH⁺) |

-continued

| # | R1 | R2 | X | Y | R3 | MS |
|---|---|---|---|---|---|---|
| 78 | 2-methylpyridin-6-yl | 5-F | —C(O)— | —CH₂— | 2-aminopyridin-4-yl | 544 (MH⁺) |
| 79 | 4-methylphenyl | 5-F | —C(O)— | —CH₂— | 2-aminopyridin-4-yl | 544 (MH⁺) |
| 80 | 3-(CO₂CH₃)phenyl | 5-F | —C(O)— | —CH₂— | 2-aminopyridin-4-yl | 587 (MH⁺) |
| 81 | H | 5-F | —C(O)— | —CH₂— | 2-aminopyridin-4-yl | 453 (MH⁺) |
| 82 | CF₃CH₂— | 5-F | —C(O)— | —CH₂— | 2-aminopyridin-4-yl | 453 (MH⁺) |
| 83 | 3,5-difluorophenyl | 5-F | —C(O)— | —CH₂— | 2-aminopyridin-4-yl | 565 (MH⁺) |
| 84 | 3,5-difluorophenyl | 5-Cl | —C(O)— | —CH₂— | pyridin-4-yl | 567 (MH⁺) |
| 85 | 3,5-difluorophenyl | 5-Cl | —C(O)— | —CH₂— | 2-aminopyridin-4-yl | 582 (MH⁺) |
| 86 | 3,5-dichlorophenyl | 5-Cl | —C(O)— | —CH₂— | 2-aminopyridin-4-yl | 614 (MH⁺) |

-continued

| Ex. | (aryl) | (R) | | | (R²) | Physical Data |
|---|---|---|---|---|---|---|
| 87 | 3,5-difluorophenyl | 5-Cl | —C(O)— | —CH(CH₃)— | 2-aminopyridin-4-yl | 596 (MH⁺) |
| 88 | pyridin-2-yl | 5-CF₃— | —C(O)— | —CH₂— | 2-aminopyridin-4-yl | 580 (MH⁺) |
| 89 | 3,5-difluorophenyl | 5-CF₃— | —C(O)— | —CH₂— | 2-aminopyridin-4-yl | 615 (MH⁺) |
| 90 | phenyl | 5-CF₃— | —C(O)— | —CH₂— | 2-aminopyridin-4-yl | 579 (MH⁺) |
| 91 | H | 5-CF₃— | —C(O)— | —CH₂— | 2-aminopyridin-4-yl | 503 |

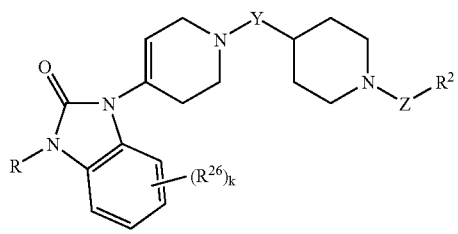

| Ex. | R | (R²⁶)ₖ | Y | Z | R² | Physical Data |
|---|---|---|---|---|---|---|
| 92 | H | H | —C(O)— | —CH₂— | pyridin-4-yl | 418 (MH⁺) |
| 93 | N(CH₃)₂—(CH₂)₂— | H | —C(O)— | —CH₂— | pyridin-4-yl | 489 (MH⁺) |
| 94 | H | H | —C(O)— | —C(O)— | 1-(1-(pyridin-4-yl)ethyl)piperidin-4-yl | 543 (MH⁺) |

-continued
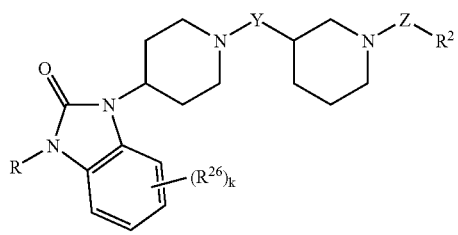
| Ex. | R | (R²⁶)ₖ | Y | Z | R² | Physical Data |
|---|---|---|---|---|---|---|
| 94 | H | 5-CF₃— | —C(O)— | —CH₂— | 3-pyridyl | 488 (MH⁺) |
| 96 | H | 5-CF₃— | —C(O)— | —CH₂— | 2-pyridyl | 488 (MH⁺) |
| 97 | H | 5-CF₃— | —C(O)— | —C(O)— | 4-pyridyl | 502 (MH⁺) |
| 98 | H | 5-CF₃— | —C(O)— | —CH₂— | 4-pyridyl N-oxide | 500 (MH⁺) |
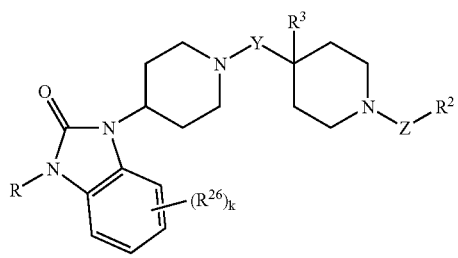
| Ex. | R | (R²⁶)ₖ | Y | R³ | Z | R² | Physical Data |
|---|---|---|---|---|---|---|---|
| 99 | H | H | —C(O)— | —CH₃ | —CH(CH₃)— | 4-pyridyl | 448 (MH⁺) |
| 100 | H | 5-CF₃— | —C(O)— | —CH₃ | —CH₂— | 4-pyridyl | 502 (MH⁺) |
| 101 | H | 5-CF₃— | —C(O)— | —OH | —CH₂— | 4-pyridyl | 504 (MH⁺) |
| 102 | CH₃O(CH₂)₂— | H | —C(O)— | F | —CH(CH₃)— | 4-pyridyl | 510 (MH⁺) |

-continued

| Ex. | | | | | | | Physical Data |
|---|---|---|---|---|---|---|---|
| 103 | H | H | —C(O)— | —CH$_3$ | —CH$_2$— | 2-bromopyridin-4-yl | 512 (MH$^+$) |
| 104 | CH$_3$O(CH$_2$)$_2$— | 5-Cl | —C(O)— | F | —CH(CH$_3$)— | pyridin-4-yl | 544 (MH$^+$) |
| 105 | CH$_3$C(O)(CH$_2$)$_2$— | 5-CF$_3$— | —C(O)— | —CH$_3$ | —CH$_2$— | pyridin-4-yl | 572 (MH$^+$) |
| 106 | CH$_3$O(CH$_2$)$_2$— | H | —C(O)— | F | —CH$_2$— | 2-aminopyrimidin-5-yl | 512 (MH$^+$) |
| 107 | CH$_3$O(CH$_2$)$_2$— | H | —C(O)— | F | —CH$_2$— | 2-aminopyridin-4-yl | 511 (MH$^+$) |
| 108 | H | 5-F | —C(O)— | F | —CH$_2$— | 2-aminopyrimidin-5-yl | 472 (MH$^+$) |

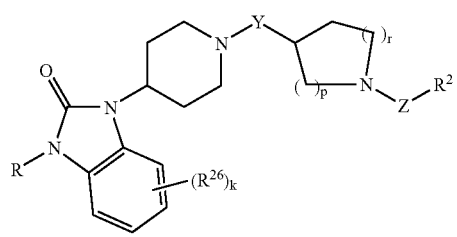

| Ex. | R | (R$^{26}$)$_k$ | Y | r | p | Z | R$^2$ | Physical Data |
|---|---|---|---|---|---|---|---|---|
| 109 | CH$_3$O(CH$_2$)$_2$— | H | —C(O)— | 0 | 1 | —CH$_2$— | pyridin-4-yl | 450 (MH$^+$) |
| 110 | CH$_3$O(CH$_2$)$_2$— | H | —C(O)— | 1 | 1 | —CH$_2$— | pyridin-4-yl | 464 (MH$^+$) |
| 111 | CH$_3$O(CH$_2$)$_2$— | H | —C(O)— | 1 | 3 | —CH$_2$— | pyridin-3-yl | 492 (MH$^+$) |

-continued

[Structure: benzimidazolone with R on one N, connected to piperidine-C(O)-piperidine-Z-R²]

| Ex. | R | Z | R² | Physical Data |
|---|---|---|---|---|
| 112 | CH₃O(CH₂)₂— | —C(O)— | 4-methylpiperidin-1-yl linked to pyridin-4-yl | 575 (MH⁺) |
| 113 | CH₃O(CH₂)₂— | —C(O)— | piperidin-4-yl with N-CH₂-pyridin-4-yl | 589 (MH⁺) |
| 114 | CH₃O(CH₂)₂— | —C(O)— | piperazin-1-yl with N-CH₂-pyridin-4-yl | 590 (MH⁺) |
| 115 | CH₃O(CH₂)₂— | —C(O)— | phenyl-N(CH₃)-pyridin-4-yl | 597 (MH⁺) |
| 116 | CH₃O(CH₂)₂— | —C(O)—N(pyridin-3-yl)—CH₂— | pyridin-4-yl | 611 (MH⁺) |
| 117 | CH₃O(CH₂)₂— | —C(O)—NH— | piperidin-4-yl with N-CH₂-pyridin-4-yl | 604 (MH⁺) |
| 118 | morpholin-4-yl-(CH₂)₃— | —C(O)— | phenyl-N(CH₃)-pyridin-4-yl | 652 (MH⁺) |
| 119 | CH₃O(CH₂)₂— | —C(O)— | piperidin-4-yl with N-CH₂-(2-aminopyridin-4-yl) | 604 (MH⁺) |

-continued
| 120 | H | —CH$_2$— | 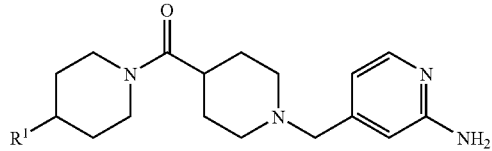 | 555 (MH$^+$) |
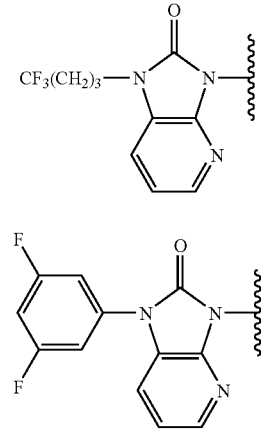
| Ex. | R$^1$ | Physical Data |
|---|---|---|
| 121 | 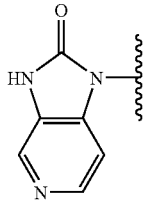 | 546 (MH$^+$) |
| 122 | 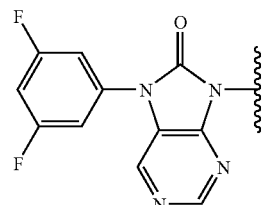 | 548 (MH$^+$) |
| 123 | 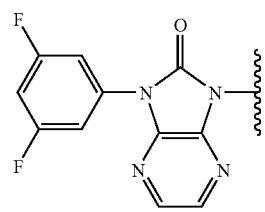 | 536 (MH$^+$) |
| 124 |  | 549 (MH$^+$) |
| 125 |  | 549 (MH$^+$) |

-continued
| 126 | 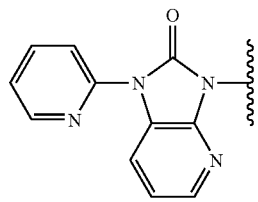 | | | 586 (MH+) |
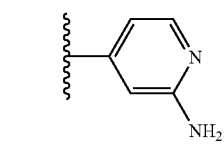
| Ex. | R¹ | R³ | R² | Physical Data |
|---|---|---|---|---|
| 127 | 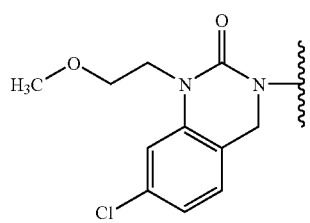 | F | 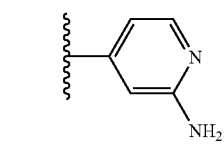 | 559 (MH+) |
| 128 | 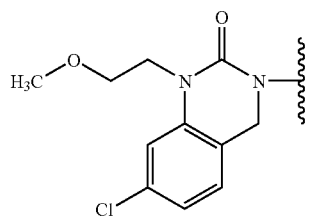 | H | 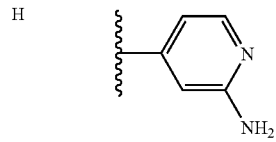 | 541 (MH+) |
| 129 | 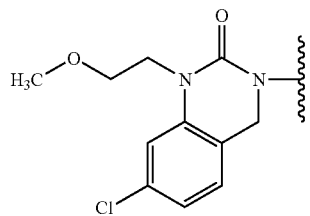 | H | 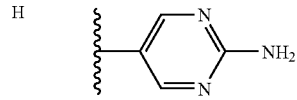 | 542 (MH+) |
| 130 | 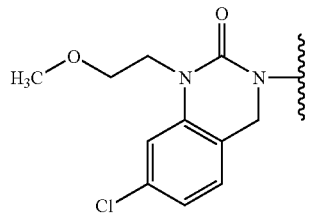 | F | 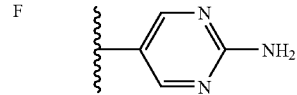 | 560 (MH+) |
| 131 | 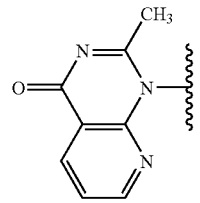 | H | 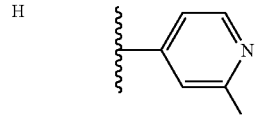 | 462 (MH+) |

| 132 | 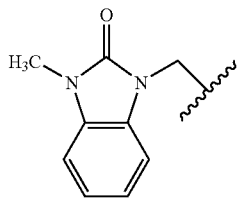 | H | 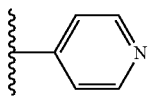 | 448 (MH+) | and

EXAMPLE 157

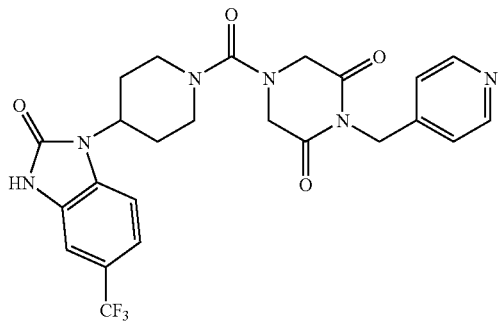

EXAMPLE 158

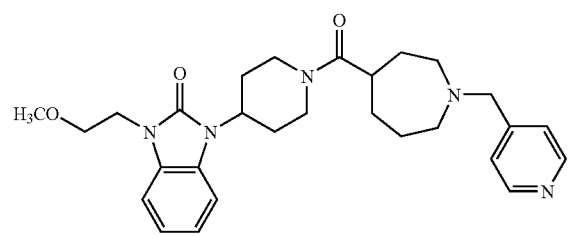

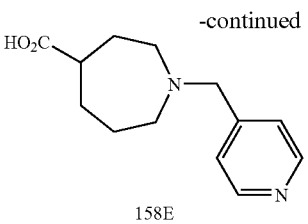

158E

In a manner similar to that described for Intermediate 3, Step D', compound 158A was converted to compound 158B.

A solution of 158B (1.7 g, 8.0 mmol) in ethylene glycol dimethyl ether (12 ml) was treated with tosylmethyl isocyanide (1.6 g, 8.0 mmol) and EtOH (1 ml), cooled to 0° C., and treated with t-BuOK (2.2 g, 16.0 mmol). The reaction mixture was stirred at 20° C. overnight, filtered through celite with EtOAc, and concentrated. Filtration through a plug of SiO$_2$ with EtOAc provided 158C as a yellow oil.

In a manner similar to that described for Intermediate 3, Step D, and then Preparation 4, Step 4, compound 158C was converted to compound 158D.

A solution of 158D (100 mg, 0.47 mmol) in EtOH (12 ml) was treated with NaOH (310 mg, 8.0 mmol) and H$_2$O (1 ml) and refluxed for 4 days. The reaction mixture was concentrated, slurried in EtOAc (20 ml), taken up in 4M HCl-dioxane and CH$_3$OH, and concentrated to provide 158E.

In a manner similar to that described in Example 1, Step G, compound 158E was converted to Example 158.

EXAMPLE 159

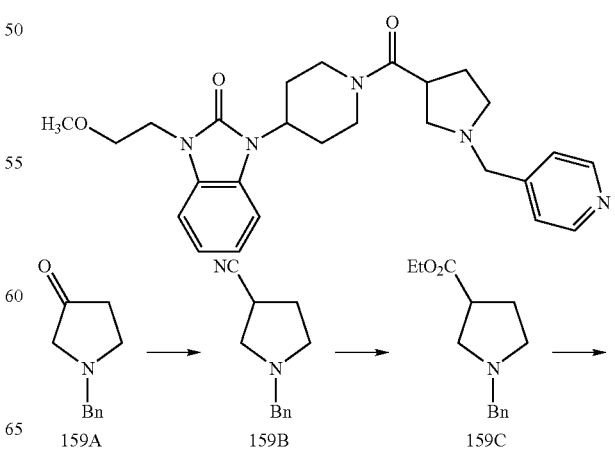

-continued

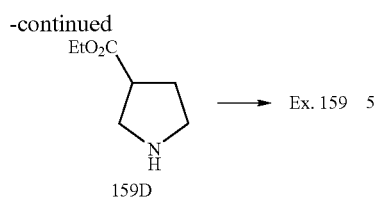

→ Ex. 159

159D

In a manner similar to that described for Example 158, compound 159A was converted to compound 159B.

A solution of 159B (1.5 g, 7.9 mmol) in EtOH (40 ml) was treated with 4M HCl-dioxane (20 ml) and stirred overnight. The reaction mixture was cooled to 0° C., treated with saturated aqueous NaHCO$_3$ until neutralized, and extracted with EtOAc. The organic layer was dried over Na$_2$SO$_4$ and concentrated. Flash chromatography (35–50% EtOAc/hexane) provided 159C (1.1 g, 58%).

A solution of 159C (210 mg, 0.85 mmol) in AcOH (10 ml) was treated with Pd(OH)$_2$ (100 mg) and stirred under H$_2$ overnight. The reaction mixture was filtered through celite and concentrated to provide 159D.

In a manner similar to that described in Preparation 4, Step 4-5 and Example 1, Step G, compound 159D was converted to compound Example 159.

Using the procedures described above for Examples 1–159, compounds of the following structure were prepared:

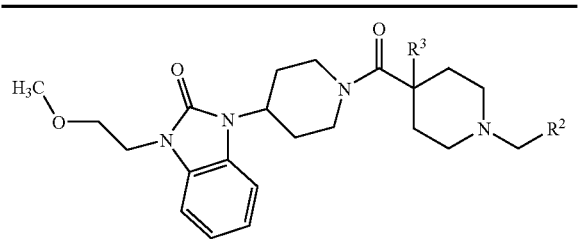

| Ex. | R$^3$ | R$^2$ | Physical Data |
|---|---|---|---|
| 160 | H | ⌇⌇-phenyl | 477 (MH$^+$) |
| 161 | F | ⌇⌇-phenyl | 495 (MH$^+$) |
| 162 | F | ⌇⌇-(4-pyridyl) | 496 (MH$^+$) |
| 163 | F | ⌇⌇-(3-furyl) | 485 (MH$^+$) |
| 164 | F | ⌇⌇-(3-thienyl) | 501 (MH$^+$) |

-continued

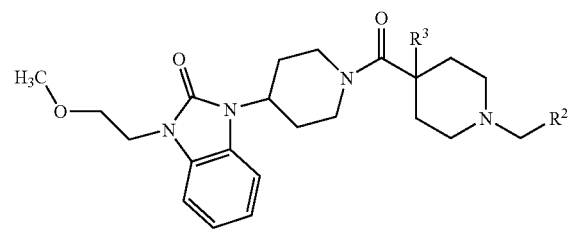

| Ex. | R$^3$ | R$^2$ | Physical Data |
|---|---|---|---|
| 165 | F | ⌇⌇-(pyridazinyl) | 497 (MH$^+$) |
| 166 | F | ⌇⌇-(2-furyl) | 485 (MH$^+$) |
| 167 | F | ⌇⌇-cyclohexyl | 501 (MH$^+$) |
| 168 | F | ⌇⌇-(2-thienyl) | 501 (MH$^+$) |
| 169 | F | ⌇⌇-(2-pyridyl) | 496 (MH$^+$) |

Using the procedures described above for Examples 1–159, compounds of the following structure can be prepared:

| Ex. | R | R$^{20}$ | R$^2$ |
|---|---|---|---|
| 170 | ⌇⌇-CH$_2$-(2-amino-pyridin-4-yl) | H | ⌇⌇-(2-amino-pyrimidin-5-yl) |

-continued

[Structure: benzimidazolone-piperidine-piperidine scaffold with substituents R, R20, R2]

| Ex. | R | R20 | R2 |
|---|---|---|---|
| 171 | cyclopropylmethyl | F | 2-aminopyrimidin-5-yl |
| 172 | 3,4-difluorophenyl | F | 2-aminopyrimidin-5-yl |
| 173 | pyrazin-2-yl | F | 2-aminopyrimidin-5-yl |
| 174 | 6-methylpyridin-2-yl | F | 2-aminopyrimidin-5-yl |
| 175 | 3,5-difluorophenyl | F | 2-aminopyrimidin-5-yl |
| 176 | pyridin-2-yl | —CF₃ | 2-aminopyrimidin-5-yl |
| 177 | CF₃(CH₂)₃— | F | 2-aminopyrimidin-5-yl |
| 178 | 2-amino-pyridin-4-ylmethyl | H | pyridazin-4-yl |
| 179 | cyclopropylmethyl | F | pyridazin-4-yl |
| 180 | 3,4-difluorophenyl | F | pyridazin-4-yl |
| 181 | pyrazin-2-yl | F | pyridazin-4-yl |
| 182 | 6-methylpyridin-2-yl | F | pyridazin-4-yl |
| 183 | 3,5-difluorophenyl | F | pyridazin-4-yl |
| 184 | pyridin-2-yl | —CF₃ | pyridazin-4-yl |
| 185 | CF₃(CH₂)₃— | F | pyridazin-4-yl |

General Procedure for H₃—Receptor Binding Assay

The source of the H₃ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM [³H]R-α-methyl histamine (8.8 Ci/mmol) or 3 nM

[$^3$H]N$^\alpha$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds of formula I have a $K_i$ within the range of about 0.1 to about 1000 nM. Preferred compounds of formula I have a $K_i$ within the range of about 0.1 to about 100 nM. More preferred compounds of formula I have a $K_i$ within the range of about 0.1 to about 20 nM. Example 1A1 has a Ki of 0.2 nM, Example 83 has a Ki of 1.0 nM, and Example 10G has a Ki of 3.9 nM.

General Procedure for rHu H$_3$ Binding Assay

[$^3$H]N$^\alpha$-methylhistamine (82 Ci/mmole) was obtained from Dupont NEN. Thioperamide was obtained from the Chemical Research Department, Schering-Plough Research Institute.

HEK-293 human embryonic kidney cells stably expressing the human histamine H$_3$ receptor were cultured in Dulbecco's modified Eagle's medium/10% fetal calf serum/penicillin (100 U/ml)/streptomycin (100 μg/ml)/Geneticin (0.5 mg/ml) at 37° C. in a humidified 5% CO$_2$ atmosphere. Cells were harvested between passages five and twenty at 37° C. in 5 mM EDTA/Hank's balanced salt solution and processed for membrane preparation. After low-speed centrifugation, ten min at 1000×g, they were put into ten volumes of ice-cold buffer and disrupted with a Polytron (PTA 35/2 tip, 30 sec at setting 6). After subsequent low-speed centrifugation, supernatant was centrifuged ten min at 50,000×g. The high-speed pellet was resuspended in the original volume of buffer, a sample was taken for protein assay (bicinchoninic acid, Pierce) and the suspension was centrifuged again at 50,000×g. Membranes were resuspended at 1 mg of protein/ml of buffer and frozen at −80° C. until use.

Membrane (15 μg of protein) was incubated with 1.2 nM [$^3$H]N$^\alpha$-methyl-histamine, without or with inhibitor compounds, in a total volume of 200 μl of buffer. Nonspecific binding was determined in the presence of 10$^{-5}$ M thioperamide. Assay mixtures were incubated for 30 min at 30° C. in polypropylene, 96-well, deep-well plates, then filtered through 0.3% polyethylenimine-soaked GF/B filters. These were washed three times with 1.2 ml of 4° C. buffer, dried in a microwave oven, impregnated with Meltilex wax scintillant and counted at 40% efficiency in a Betaplate scintillation counter (Wallac).

IC$_{50}$ values were interpolated from the data or were determined from curves fit to the data with Prism nonlinear least squares curve-fitting program (GraphPad Software, San Diego, Calif.). $K_i$ values were determined from IC$_{50}$ values according to the Cheng and Prusoff equation.

In this specification, the term "at least one compound of formula I" means that one to three different compounds of formula I may be used in a pharmaceutical composition or method of treatment. Preferably one compound of formula I is used. Similarly, "at least one H$_1$ receptor antagonist" means that one to three different H$_1$ antagonists may be used in a pharmaceutical composition or method of treatment. Preferably, one H$_1$ antagonist is used.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 350 mg, preferably from about 1 mg to about 150 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of H$_3$ antagonist and H$_1$ antagonist compounds, the two active components may be co-administered simultaneously or sequentially, or a single pharmaceutical composition comprising a H$_3$ antagonist and an H$_1$ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the H$_1$ antagonist can be determined from published material, and may range from 1 to 1000 mg per dose.

When separate H$_3$ and H$_1$ antagonist pharmaceutical compositions are to be administered, they can be provided in a kit comprising in a single package, one container comprising an H₃ antagonist in a pharmaceutically acceptable carrier, and a separate container comprising an H₁ antagonist in a pharmaceutically acceptable carrier, with the H₃ and H₁ antagonists being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula

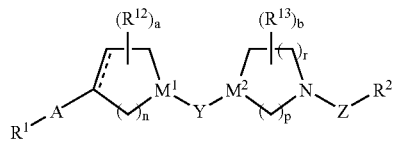

or a pharmaceutically acceptable salt or solvate thereof, wherein:

the dotted line represents an optional double bond;
a is 0 to 3;
b is 0 to 3;
n is 2;
r is 1 and p is 2; or r is 2 and p is 1;
A is a bond or $C_1$–$C_6$ alkylene;
$M^1$ is N;
$M^2$ is $C(R^3)$;
Y is —C(=O)—, —C(=O)NR⁴—, —C(=O)CH₂—, —CH₂(C=O)—, —SO$_{1-2}$—,
Z is a bond, $C_1$–$C_6$ alkylene, $C_1$–$C_6$ alkenylene, —C(=O)—, —CH(CN)—, or —CH₂C(=O)NR⁴—;
$R^1$ is

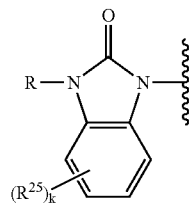 , 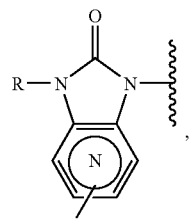 ,

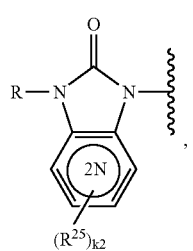 , 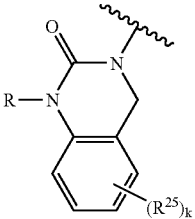

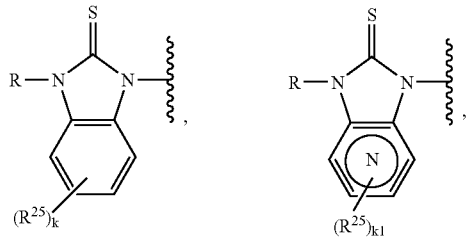 , 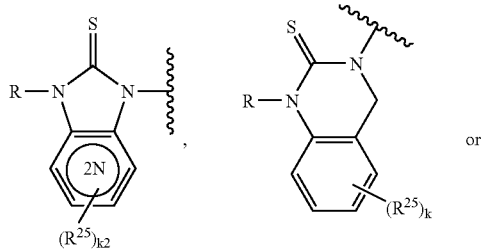 ,

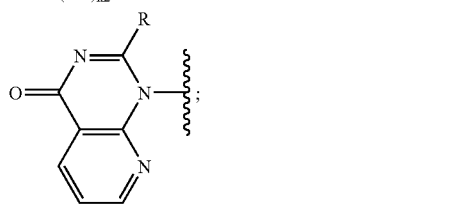

k is 0, 1, 2, 3 or 4;
k1 is 0, 1, 2 or 3;
k2 is 0, 1 or 2;
R is H, $C_1$–$C_6$ alkyl, hydroxy-($C_2$–$C_6$)alkyl-, halo-($C_1$–$C_6$)alkyl-, halo-($C_1$–$C_6$)-alkoxy-($C_1$–$C_6$)alkyl-, $R^{29}$—O—C(O)—($C_1$–$C_6$)alkyl-, ($C_1$–$C_6$)alkoxy-($C_1$–$C_6$)alkyl-, N($R^{30}$)($R^{31}$)—($C_1$–$C_6$)alkyl-, ($C_1$–$C_6$)alkoxy-($C_1$–$C_6$)alkoxy-($C_1$–$C_6$)alkyl-, $R^{32}$-aryl, $R^{32}$-aryl($C_1$–$C_6$)alkyl-, $R^{32}$-aryloxy($C_1$–$C_6$)alkyl-, $R^{32}$-heteroaryl, $R^{32}$-heteroaryl($C_1$–$C_6$)alkyl-, ($C_3$–$C_6$)cycloalkyl, ($C_3$–$C_6$)cycloalkyl($C_1$–$C_6$)alkyl-, N($R^{30}$)($R^{31}$)—C(O)—($C_1$–$C_6$)alkyl-, or heterocycloalkyl($C_1$–$C_6$)alkyl-;

R² is a six-membered heteroaryl ring having 1 or 2 heteroatoms independently selected from N or N—O, with the remaining ring atoms being carbon; a five-membered heteroaryl ring having 1, 2, 3 or 4 heteroatoms independently selected from N, O or S, with the remaining ring atoms being carbon; $R^{32}$-quinolyl; heterocycloalkyl; ($C_3$–$C_6$)cycloalkyl; ($C_1$–$C_6$)alkyl; hydrogen;

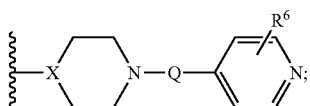

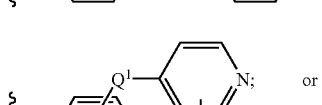

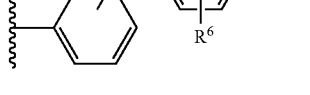 or 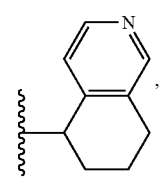

wherein said six-membered heteroaryl ring or said five-membered heteroaryl ring is optionally substituted by $R^6$;

X is CH or N;

Q is a bond or $C_1$–$C_6$ alkylene;

$Q^1$ is a bond, $C_1$–$C_6$ alkylene or —N($R^4$)—;

$R^3$ is H, halogen, $C_1$–$C_6$ alkyl, —OH or ($C_1$–$C_6$)alkoxy;

$R^4$ is independently selected from the group consisting of hydrogen, $C_1$–$C_6$ alkyl, $C_3$–$C_6$ cycloalkyl, ($C_3$–$C_6$)cycloalkyl($C_1$–$C_6$)alkyl, $R^{33}$-aryl, $R^{33}$-aryl($C_1$–$C_6$)alkyl, and $R^{32}$-heteroaryl;

$R^5$ is hydrogen, $C_1$–$C_6$ alkyl, —C(O)$R^{20}$, —C(O)$_2R^{20}$, —C(O)N($R^{20}$)$_2$ or ($C_1$–$C_6$)alkyl-$SO_2$—;

or $R^4$ and $R^5$, together with the nitrogen to which they are attached, form an azetidinyl, pyrrolidinyl, piperidinyl, piperazinyl or morpholinyl ring;

$R^6$ is 1 to 3 substituents independently selected from the group consisting of —OH, halogen, $C_1$–$C_6$ alkyl-, $C_1$–$C_6$ alkoxy, $C_1$–$C_6$ alkylthio, —$CF_3$, —$NR^4R^5$, $NO_2$, —$CO_2R^4$, —CON($R^4$)$_2$, —$CH_2$—$NR^4R^5$, —CN,

[structures shown]

or 2 $R^6$ substituents together on the same carbon are =O;

$R^{12}$ is independently selected from the group consisting of $C_1$–$C_6$ alkyl, hydroxy, $C_1$–$C_6$ alkoxy, or fluoro, provided that when $R^{12}$ is hydroxy or fluoro, then $R^{12}$ is not bound to a carbon adjacent to a nitrogen; or two $R^{12}$ substituents together form a $C_1$ to $C_2$ alkyl bridge from one ring carbon to another non-adjacent ring carbon; or $R^{12}$ is =O;

$R^{13}$ is independently selected from the group consisting of $C_1$–$C_6$ alkyl, hydroxy, $C_1$–$C_6$ alkoxy, or fluoro, provided that when $R^{13}$ is hydroxy or fluoro then $R^{13}$ is not bound to a carbon adjacent to a nitrogen; or two $R^{13}$ substituents together form a $C_1$ to $C_2$ alkyl bridge from one ring carbon to another non-adjacent ring carbon; or $R^{13}$ is =O;

$R^{20}$ is independently selected from the group consisting of hydrogen, $C_1$–$C_6$ alkyl, or aryl, wherein said aryl group is optionally substituted with from 1 to 3 groups independently selected from halogen, —$CF_3$, —$OCF_3$, hydroxyl, or methoxy; or when two $R^{20}$ groups are present, said two $R^{20}$ groups taken together with the nitrogen to which they are bound can form a five or six membered heterocyclic ring;

$R^{22}$ is $C_1$–$C_6$ alkyl, $R^{34}$-aryl or heterocycloalkyl;

$R^{24}$ is H, $C_1$–$C_6$ alkyl, —$SO_2R^{22}$ or $R^{34}$-aryl;

$R^{25}$ is independently selected from the group consisting of $C_1$–$C_6$ alkyl, —CN, —$NO_2$, halogen, —$CF_3$, —OH, $C_1$–$C_6$ alkoxy, ($C_1$–$C_6$)alkyl-C(O)—, aryl-C(O)—, N($R^4$)($R^5$)—C(O)—, N($R^4$)($R^5$)—S(O)$_{1-2}$—, halo-($C_1$–$C_6$)alkyl- or halo-($C_1$–$C_6$)alkoxy-($C_1$–$C_6$)alkyl-;

$R^{29}$ is H, $C_1$–$C_6$ alkyl, $R^{35}$-aryl or $R^{35}$-aryl($C_1$–$C_6$)alkyl-;

$R^{30}$ is H, $C_1$–$C_6$ alkyl-, $R^{35}$-aryl or $R^{35}$-aryl($C_1$–$C_6$)alkyl-;

$R^{31}$ is H, $C_1$–$C_6$ alkyl-, $R^{35}$-aryl, $R^{35}$-aryl($C_1$–$C_6$)alkyl-, ($C_1$–$C_6$)alkyl-C(O)—, $R^{35}$-aryl-C(O)—, N($R^4$)($R^5$)—C(O)—, ($C_1$–$C_6$)alkyl-S(O)$_2$— or $R^{35}$-aryl-S(O)$_2$—;

or $R^{30}$ and $R^{31}$ together are —($CH_2$)$_{4-5}$—, —($CH_2$)$_2$—O—($CH_2$)$_2$— or —($CH_2$)$_2$—N($R^{29}$)—($CH_2$)$_2$— and form a ring with the nitrogen to which they are attached;

$R^{32}$ is 1 to 3 substituents independently selected from the group consisting of H, —OH, halogen, $C_1$–$C_6$ alkyl, $C_1$–$C_6$ alkoxy, —$SR^{22}$, —$CF_3$, —$OCF_3$, —$OCHF_2$, —$NR^{37}R^{38}$, —$NO_2$, —$CO_2R^{37}$, —CON($R^{37}$)$_2$, —S(O)$_2R^{22}$, —S(O)$_2$N($R^{20}$)$_2$, —N($R^{24}$)S(O)$_2R^{22}$, —CN, hydroxy-($C_1$–$C_6$)alkyl- and —$OCH_2CH_2OR^{22}$;

$R^{33}$ is 1 to 3 substituents independently selected from the group consisting of $C_1$–$C_6$ alkyl, halogen, —CN, —$NO_2$, —$OCHF_2$ and —O—($C_1$–$C_6$)alkyl;

$R^{34}$ is 1 to 3 substituents independently selected from the group consisting of H, halogen, —$CF_3$, —$OCF_3$, —OH and —$OCH_3$, $R^{35}$ is 1 to 3 substituents independently selected from hydrogen, halo, $C_1$–$C_6$ alkyl, hydroxy, $C_1$–$C_6$ alkoxy, phenoxy, —$CF_3$, —N($R^{36}$)$_2$, —$COOR^{20}$ and —$NO_2$;

$R^{36}$ is independently selected form the group consisting of H and $C_1$–$C_6$ alkyl;

$R^{37}$ is independently selected from the group consisting of hydrogen, $C_1$–$C_6$ alkyl, $C_3$–$C_6$ cycloalkyl, ($C_3$–$C_6$)cycloalkyl($C_1$–$C_6$)alkyl, $R^{33}$-aryl, $R^{33}$-aryl($C_1$–$C_6$)alkyl, and $R^{32}$-heteroaryl; and $R^{38}$ is hydrogen, $C_1$–$C_6$ alkyl, —C(O)$R^{20}$, —C(O)$_2R^{20}$, —C(O)N($R^{20}$)$_2$ or ($C_1$–$C_6$)alkyl-$SO_2$—;

or $R^{37}$ and $R^{38}$, together with the nitrogen to which they are attached, form an azetidinyl, pyrrolidinyl, piperidinyl, piperazinyl or morpholinyl ring.

2. A compound of claim 1 wherein A is a bond, a is 0, and the optional double bond is not present.

3. A compound of claim 2 wherein $M^2$ is C($R^3$) wherein $R^3$ is hydrogen or halogen, b is 0; r is 1 and p is 2.

4. A compound of claim 3 wherein Z is straight or branched $C_1$–$C_3$ alkyl.

5. A compound of claim 4 wherein $R^2$ is a six-membered heteroaryl ring, optionally substituted with one $R^6$ substituent.

6. A compound of claim 5 wherein $R^2$ is pyridyl, pyrimidyl or pyridazinyl, each optionally substituted with halogen or —$NR^4R^5$ wherein $R^4$ and $R^5$ are independently selected from the group consisting of H and ($C_1$–$C_6$)alkyl, or $R^4$ and $R^5$ together with the nitrogen to which they are attached, form a pyrrolidinyl, piperidinyl or morpholinyl ring.

7. A compound of claim 6 wherein $R^1$ is R-substituted benzimidazolone, wherein R is H, ($C_1$–$C_6$)alkyl, ($C_1$–$C_6$) alkoxy($C_1$–$C_6$)alkyl, $R^{32}$-aryl, $R^{32}$-heteroaryl or heterocycloalkyl($C_1$–$C_6$)alkyl.

8. A compound of claim 7 wherein R is H, —$CH_3$, phenyl, 4-fluorophenyl, $CH_3$—O—($CH_2$)$_2$—,

[structures shown]

9. A compound of claim 7 wherein $R^{25}$ is halogen or —$CF_3$ and k is 0 or 1.

10. A compound of claim 1 selected from the group consisting of
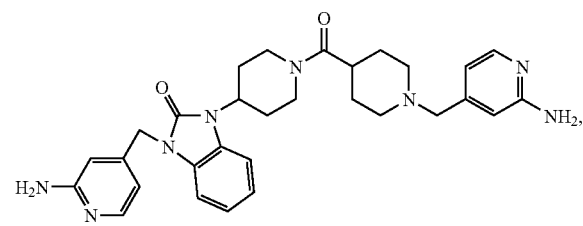
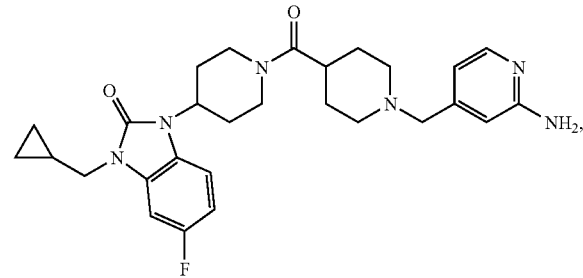
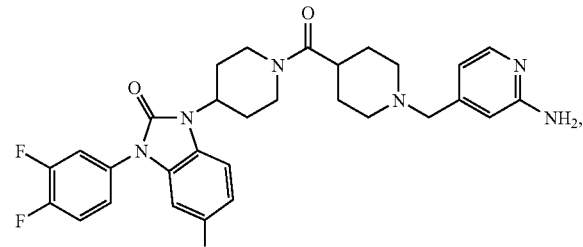
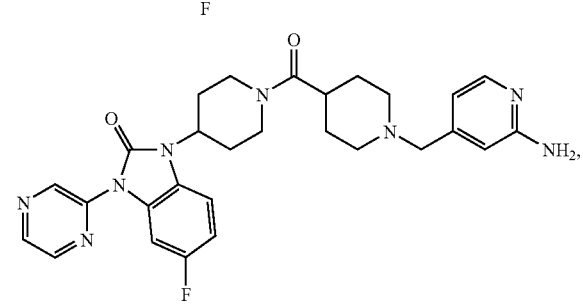
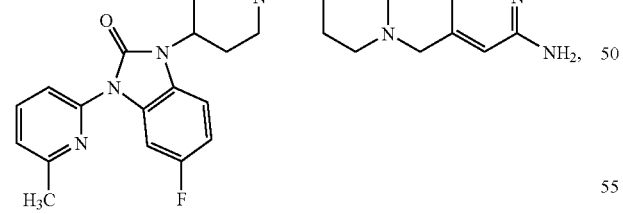
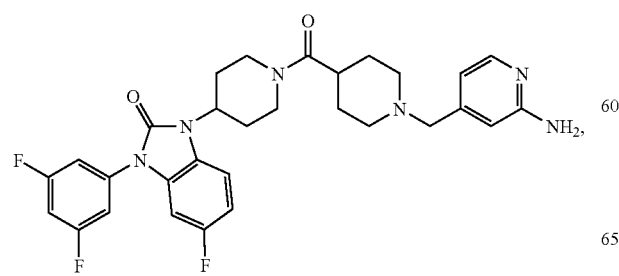
-continued
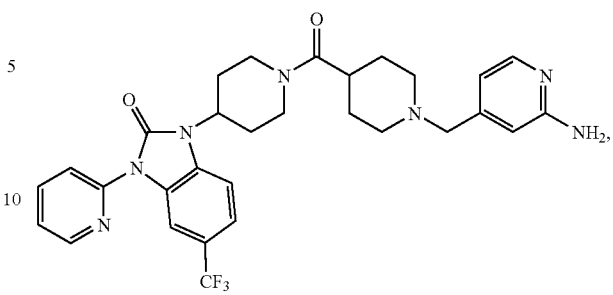
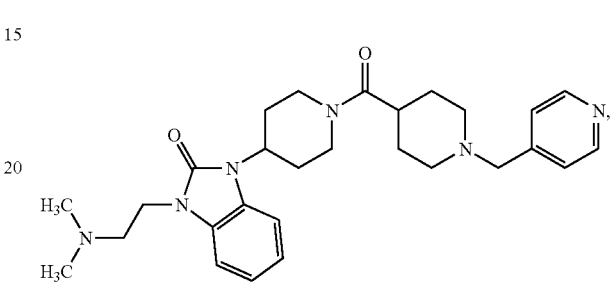
and
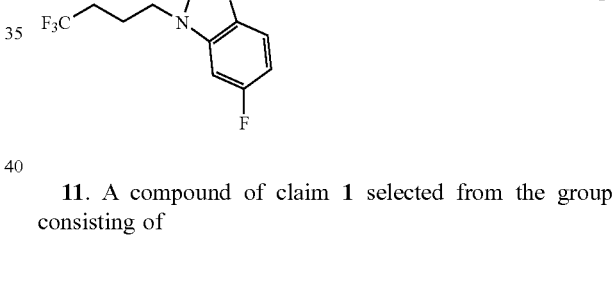
11. A compound of claim 1 selected from the group consisting of
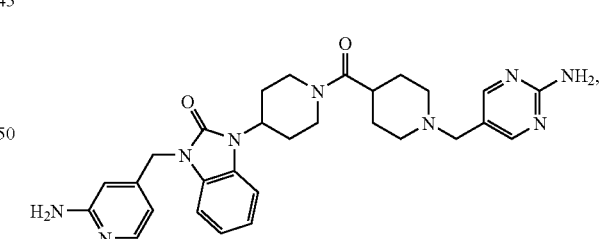
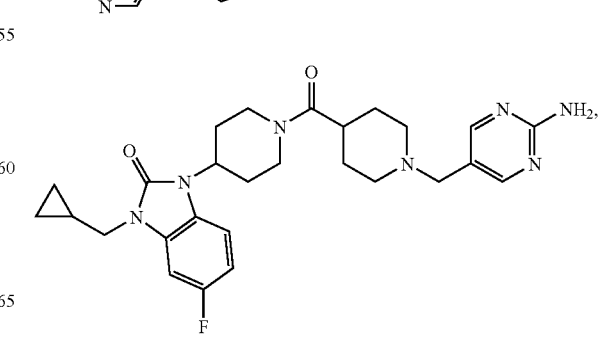

-continued
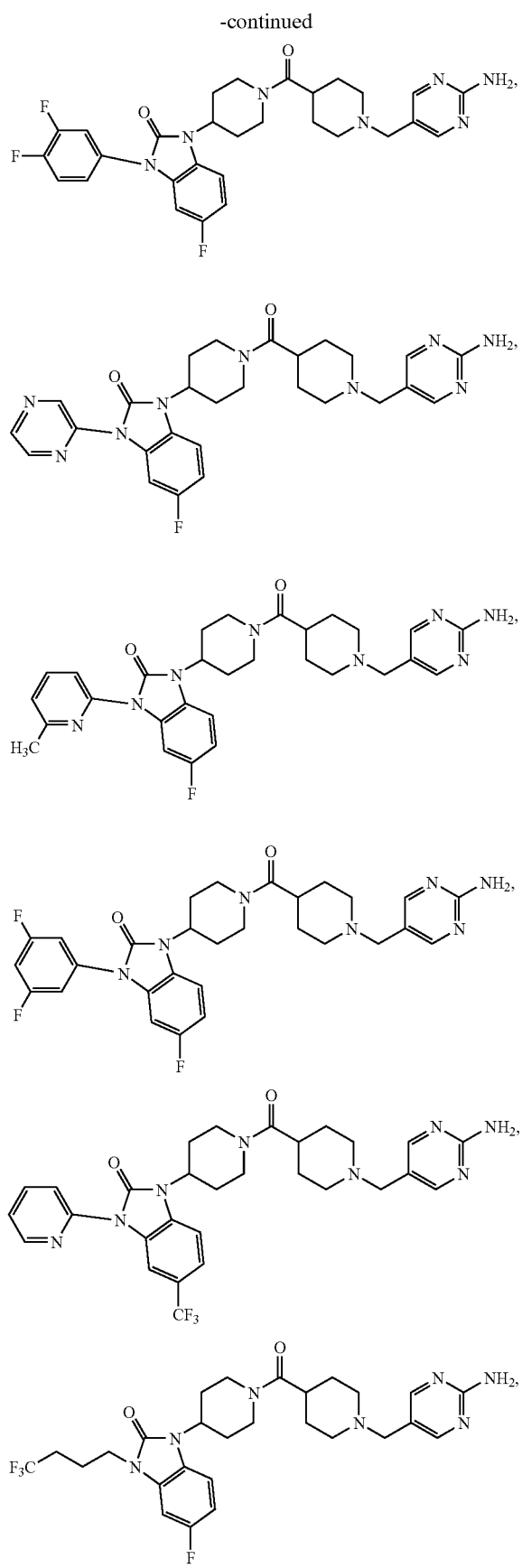
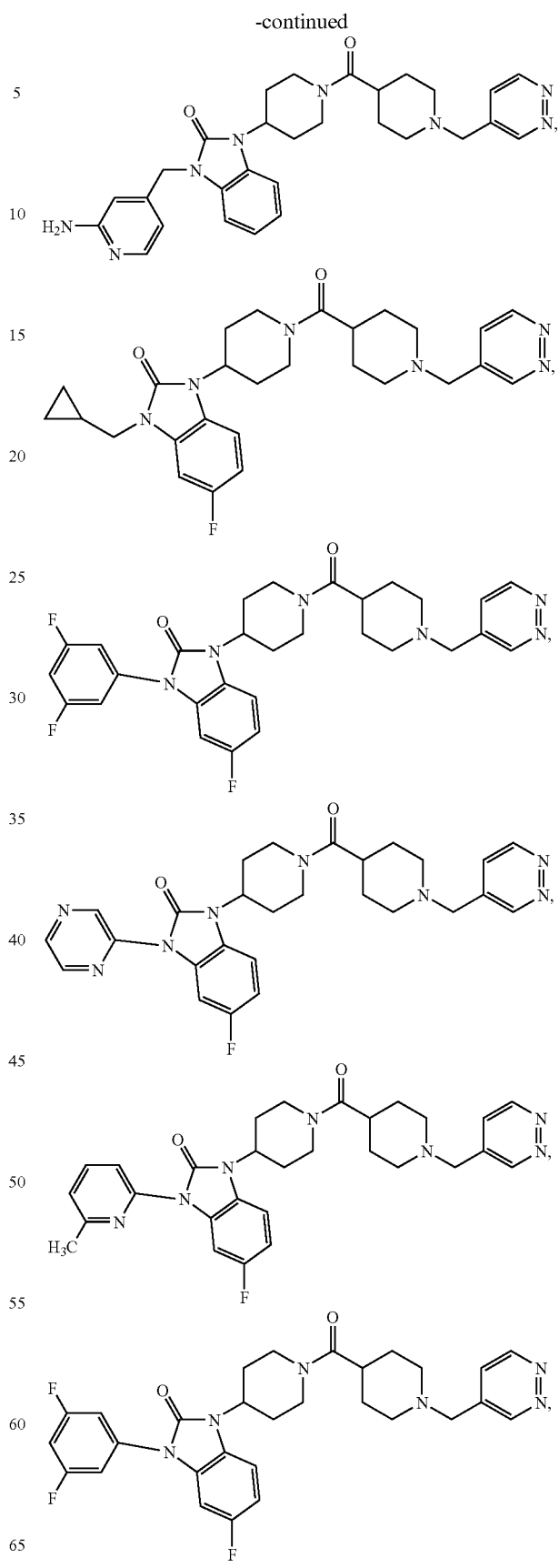

-continued

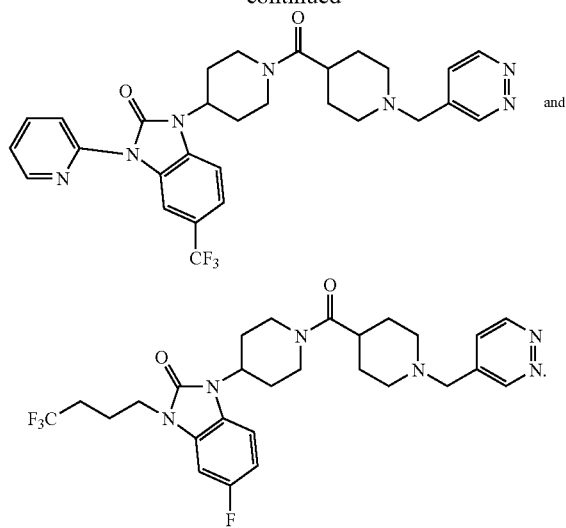

and

12. A pharmaceutical composition comprising an effective amount of a compound of claim 1 and a pharmaceutically effective carrier.

13. A method of treating nasal congestion, obesity, somnolence, narcolepsy, attention deficit hyperactivity disorder, Alzheimer's disease or schizophrenia, comprising administering to a patient in need of such treatment an effective amount of a compound of claim 1.

14. A pharmaceutical composition comprising an effective amount of a compound of claim 1, and an effective amount of $H_1$ receptor antagonist, and a pharmaceutically effective carrier.

15. A method of treating nasal congestion comprising administering to a patient in need of such treatment an effective amount of a compound of claim 1 in combination with an effective amount of an $H_1$ receptor antagonist.

16. The method of claim 15 wherein said $H_1$ receptor antagonist is selected from the group consisting of astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine.

17. The method of claim 16 wherein said $H_1$ receptor antagonist is selected from the group consisting of loratadine, descarboethoxyloratadine, fexofenadine and cetirizine.

18. The method of claim 17 wherein said $H_1$ receptor antagonist is loratadine or descarboethoxyloratadine.

* * * * *

UNITED STATES PATENT AND TRADEMARK OFFICE
CERTIFICATE OF CORRECTION

PATENT NO. : 7,220,735 B2  Page 1 of 1
APPLICATION NO. : 10/414943
DATED : May 22, 2007
INVENTOR(S) : Pauline C. Ting It is certified that error appears in the above-identified patent and that said Letters Patent is hereby corrected as shown below:

Claim 1, Column 139, line 13: Replace "$(R_{20})$" with -- $(R^{20})$ --.

Claim 1, Column 140, line 31: Replace "$(R_{20})$" with -- $(R^{20})$ --.

Signed and Sealed this

Thirty-first Day of July, 2007

JON W. DUDAS
*Director of the United States Patent and Trademark Office*